United States Patent [19]

Massey et al.

[11] Patent Number: 5,716,781
[45] Date of Patent: Feb. 10, 1998

[54] METHOD OF CALIBRATION OF AN ELECTROCHEMILUMINESCENT ASSAY SYSTEM

[75] Inventors: Richard J. Massey, Rockville; Michael J. Powell, Gaithersburg; Walter J. Dressick, Gaithersburg; Jonathan K. Leland, Gaithersburg, all of Md.; Janel K. Hino, Arlington, Va.; Mohindar S. Poonian; Leopoldo Della Ciana, both of Gaithersburg, Md.

[73] Assignee: Igen International Inc., Gaithersburg, Md.

[21] Appl. No.: 470,247

[22] Filed: Jun. 6, 1995

Related U.S. Application Data

[62] Division of Ser. No. 227,898, Apr. 15, 1994, Pat. No. 5,591,581, which is a continuation of Ser. No. 533,931, Jun. 5, 1990, abandoned, which is a continuation of Ser. No. 117,017, Nov. 4, 1987, abandoned, which is a continuation-in-part of Ser. No. 858,354, Apr. 30, 1986, abandoned.

[51] Int. Cl.[6] .............................. C12Q 1/00; C12Q 1/70; C12Q 1/68; G01N 33/48
[52] U.S. Cl. .................. 435/6; 435/4; 435/5; 435/7.1; 435/7.2; 435/287; 435/291; 435/810; 436/63; 436/501; 536/24.3; 536/24.31; 536/24.32; 536/26.6
[58] Field of Search .................... 435/4, 5, 6, 7.1, 435/7.2, 287, 291, 810; 436/501, 63; 536/24.3, 24.31, 24.32, 26.6; 935/76, 77, 78

[56] References Cited

U.S. PATENT DOCUMENTS 4,390,274  6/1983  Berthold et al. ................... 356/36

(List continued on next page.)

FOREIGN PATENT DOCUMENTS 0137457  4/1985  European Pat. Off. .

OTHER PUBLICATIONS

Weber, S.G., et al., "Photoelectroanalytical Chemistry: Possible Interference in Serum and Selective Detection of Tris (2,2'-bypyridine) ruthenium (II) in the Presence of Interferents," *Clinical Chemistry* 29:1665–1672 (1983).

(List continued on next page.)

*Primary Examiner*—Ardin H. Marschel
*Assistant Examiner*—Jezia Riley
*Attorney, Agent, or Firm*—Curtis, Morris & Safford, P.C.; Barry Evans, Esq.; David Rubin, Esq.

[57] ABSTRACT

Electrochemiluminiscent moieties having the formula

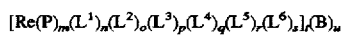

wherein
P is a polydentate ligand of Re;
$L^1, L^2, L^3, L^4, L^5$ and $L^6$ are ligands of Re, each of which may be the same as or different from each other ligand;
B is a substance which is a ligand of Re or is conjugated to one or more of P, $L^1, L^2, L^3, L^4, L^5$ or $L^6$;
m is an integer equal to or greater than 1;
each of n, o, p, q, r and s is zero or an integer;
t is an integer equal to or greater than 1; and
u is an integer equal to or greater than 1;
P, $L^1, L^2, L^3, L^4, L^5$, $L^6$ and B being of such composition and number that the chemical moiety can be induced to emit electromagnetic radiation and the total number of bonds to Re provided by the ligands of Re being equal to the coordination of Re
are disclosed.

Qualitative and quantitative electrochemiluminescent assays for analytes of interest present in multicomponent liquids using these moieties are disclosed. These methods comprise contacting a sample with a reagent labeled with an electrochemiluminescent chemical moiety containing rhenium and capable of combining with the analyte of interest, exposing the resulting sample to chemical, electrochemical, or electromagnetic energy and detecting electromagnetic radiation emitted by the electrochemiluminescent chemical moiety.

12 Claims, 3 Drawing Sheets

U.S. PATENT DOCUMENTS

| | | | |
|---|---|---|---|
| 4,412,064 | 10/1983 | Hinman | 528/9 |
| 4,652,440 | 3/1987 | Paik et al. | 424/1.1 |
| 4,659,839 | 4/1987 | Nicolotti et al. | 548/546 |
| 4,707,440 | 11/1987 | Stavrianopoulos | 435/6 |
| 4,745,076 | 5/1988 | Muller et al. | 436/537 |

OTHER PUBLICATIONS

Rubinstein, I., and Bard, A.J., "Electrogenerated Chemiluminescence. 37, Aqueous ECL Systems Based on Ru (2,2'–bypyridine)$_3{}^{2+}$ and Oxalate or Organic Acids," *J. Am. Chem. Soc. 103*:512–516 (1981).

White, H.S., and Bard, A.J., "Electrogenerated Chemiluminescence. 41. Electrogenerated Chemiluminescence and Chemiluminescence of the Ru (2,2–bpy)$_3{}^{+2}$–S$_2$O$_8{}^{-2}$ System in Acetonitrile–Water Solutions," *J. Am. Chem. Soc. 104*:6891 (1982).

Curtis et al., "Chemiluminescence: A New Method for Detecting Fluorescent Compounds Separated by Thin Layer Chromatography," *J. Chromatography 134*:343–350 (1977).

Sprinschnik, G., et al., "Preparation and Photochemical Reactivity of Surfactant Ruthenium (II) Complexes in Monolayer Assemblies and at Water–Solid Interface," *J. Am. Chem. Soc. 99*:4947–4954 (1977).

Minnich, S.A., et al., "Enzyme Immunoassay for Detection of Salmonellae in Foods," *Appln. and Environ. Micro. 43*: (1982), pp. 877–883.

Mattingly, J.A., "An Enzyme Immunoassay for the Detection of All Salmonella Using a Combination of a Myleloma Protein and a Hybridoma Antibody," *J. Immunol. Meth. 73*:147–156 (1984).

Thompson, N.E., et al., "Detection of Staphylococcal enterotoxins by enzyme–linked immunosorbent assays and radio–immunoassays: Comparison of monoclonal and polyclonal antibody systems," *Appln. and Environ. Micro.*, submitted publication.

Clark, H.F., Geldreich, E.E., Lester, H.L., and Kabler, P.W., "The membrane filter in sanitary microbiology", *Public Health Rep. 66*:951–957 (1951).

Feng, P., and Hartman, P.A., "Fluorogenic assays for immediate confirmation of *Escherichia coli*," *Appl. Environ. Microbiol. 43*:1320–1329 (1982).

Olson, B.H., "Enhanced accuracy of coliform testing in seawater by modification of the most–probable–number method," *Appl. Environ. Microbiol. 36*:438–444 (1978).

Presswood, W.G. and Strong, D.K., "Modification of mFC medium by eliminating rosolic acid," *Appl. Environ. Microbiol. 36*:90–94 (1978).

Warr, G.W., and Marchalonis, J.J., "Purification of Antibodies," *Antibody as a Tool*, J. Wiley and Sons, New York, 59–96 (1982).

Maniatis, T., Fritsch, E.F., and Sambrook, J., *Molecular Cloning: A Laboratory Manual*, 150–160, Cold Spring Harbor Press, Cold Spring Harbor, New York (1982).

Caspar J. V., Meyer, T. J., "Application of the Energy Law to Nonradiative, Excited State Decay", *J. Phys. Chem. 87*, 952–957 (1983).

Westmoreland T. D., Bozec H. L., Murray, R. W., Meyer, T. J., "Multiple–State Emission and Intramolecular Electron–Transfer Quenching in Rhenium(I) Bipyridine Based Chromophore–Quencher Complexes", *J. Am. Chem. Soc. 105*, 5952–5954 (1983).

Mitra, T., Bhadra, A., Sen, S., Sen, B. K., Bandyopadhyay, P., "Nitrosyl Rhenium Complexes. Synthesis, Properties and Structure of Oxalato Derivatives", *Chemical Abstracts 99*, 151025g (1983).

Kalyanasundaram, K., "Luminescence and Redox Reactions of the Metal–to–Ligand Charge–Transfer Excited State of Tricarbonyl Chloro–(polypyridyl)rhenium(I) Complexes", *Chemical Abstracts 99*, 58729t (1987).

Salman, O. A. and Drickamer, H. G., "The Effect of Pressure and Freezing on Luminescence. II. Re(I) Metal Complexes", *J. Chem. Phys. 77*, 3337–3343 (1982).

Ege, D., Becker, W. G., Bard, A. J., "Electrogenerated Chemiluminescent Determination of Ru(bpy)$_3{}^{2+}$ at low levels", *J. Anal. Chem. 56*, 2413–2417 (1984).

Hector D. Abruña "Electrogenerated Chemiluminescence of Bipyridine and Phenauthroline Complexes of Osmium" J. Electroanal. Chem. 175 (1984) pp. 321–326.

Tokel–Takvorian et al. "Electrogenerated Chemiluminescence. XIII. Electrochemical and Electrogenerated Chemiluminescence Studies of Ruthenium Chelates", J. Am. Chem. Soc., 95 (1973) p. 6582.

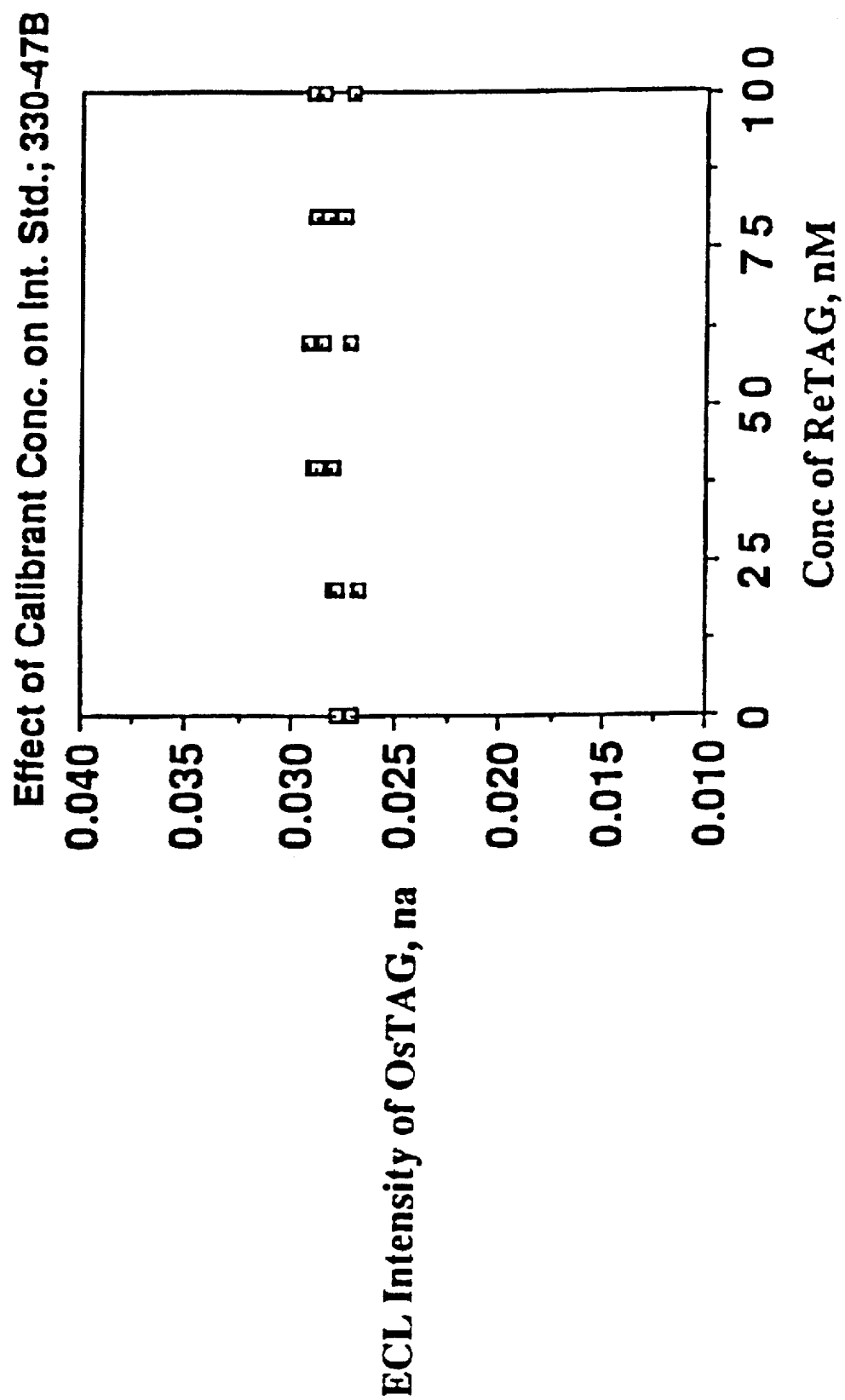

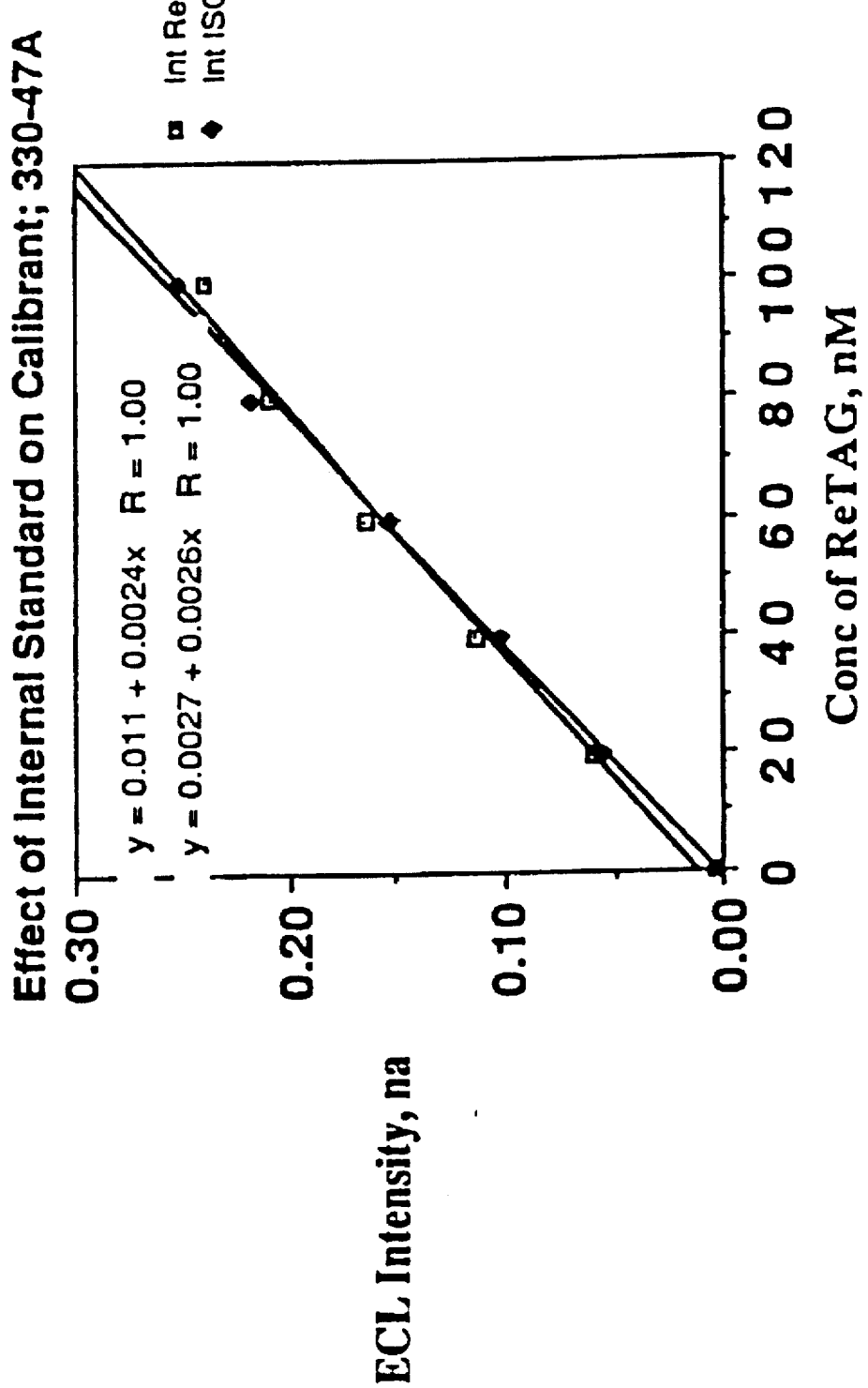

METHOD OF CALIBRATION OF AN ELECTROCHEMILUMINESCENT ASSAY SYSTEM

This application is a division of application Ser. No. 08/227,898 filed Apr. 15, 1994, now U.S. Pat. No. 5,591,581, which is a continuation of application Ser. No. 07/533,931 filed Jun. 5, 1990, now abandoned, which in turn is a continuation of application Ser. No. 07/117,017 filed Nov. 4, 1987, now abandoned. Application Ser. No. 07/117,017 filed Nov. 4, 1987, now abandoned, is a continuation-in-part of application Ser. No. 06/858,354, filed Apr. 30, 1986, now abandoned, and a continuation-in-part of PCT application U.S. No. 87/00987, filed Apr. 30, 1987, which in turn is a continuation in part of application Ser. No. 06/858,354, filed Apr. 30, 1986, now abandoned.

The invention relates to electrochemiluminescent chemical moieties which include the metal rhenium. The rhenium-containing chemical moieties and complexes thereof disclosed in this application offer several advantages over tris-2,2'-bipyridine ruthenium (II) and related complexes proposed for use in assay systems. These advantages include: (1) emission quantum efficiencies ($\phi_r$) which are generally more favorable than those noted for tris-2,2'-bipyridine ruthenium (II) derivatives; (2) the ability to select the properties of the metal-to-ligand charge-transfer (MLCT) excited state within a wider range of values than are available for tris-2,2'-bipyridine ruthenium (II) derivatives; and (3) simplified and more economical methods of synthesis because both bipyridyl and nonbipyridyl derivatives can be used to conjugate an analyte of interest to the complex.

BACKGROUND OF THE INVENTION

Several publications are referenced in this application by Arabic numerals within parentheses. Full citations for these references are found at the end of the specification immediately preceding the claims. The disclosures of these publications are incorporated by reference into this application in order to more fully describe the state of the art to which this invention pertains.

There is a continuous and expanding need for rapid, highly specific methods of detecting and quantifying chemical, biochemical, and biological substances. Of particular value are methods for measuring small quantities of pharmaceuticals, metabolites, microorganisms and other materials of diagnostic value. Examples of such materials include narcotics and poisons, drugs administered for therapeutic purposes, hormones, pathogenic microorganisms and viruses, antibodies, metabolites, enzymes and nucleic acids.

The presence of these materials can often be determined by binding methods which exploit the high degree of specificity which characterizes many biochemical and biological systems. Frequently used methods are based on, for example, antigen-antibody systems, nucleic acid hybridization techniques, and protein-ligand systems. In these methods, the existence of a complex of diagnostic value is typically indicated by the presence or absence of an observable "label" which has been attached to one or more of the complexing materials. The specific labeling method chosen often dictates the usefulness and versatility of a particular system for detecting a material of interest. A preferred label should be inexpensive, safe, and capable of being attached efficiently to a wide variety of chemical, biochemical, and biological materials without changing the important binding characteristics of those materials. The label should give a highly characteristic signal, and should be rarely, and preferably never, found in nature. The label should be stable and detectable in aqueous systems over periods of time ranging up to months. Detection of the label should be rapid, sensitive, and reproducible without the need for expensive, specialized facilities or personnel. Quantification of the label should be relatively independent of variables such as temperature and the composition of the mixture to be assayed. Most advantageous are labels which can be used in homogeneous systems, i.e., systems in which separation of the complexed and uncomplexed labeled material is not necessary. This is possible if the detectability of the label is modulated when the labeled material is incorporated into a specific complex.

A wide variety of labels have been developed, each with particular advantages and disadvantages. For example, radioactive labels are quite versatile, and can be detected at very low concentrations. However, they are expensive, hazardous, and their use requires sophisticated equipment and trained personnel. Furthermore, the sensitivity of radioactive labels is limited by the fact that the detectable event can, in its essential nature, occur only once per radioactive atom in the labeled material. Moreover, radioactive labels cannot be used in homogeneous methods. Thus, there is wide interest in nonradioactive labels. These include molecules observable by spectrophotometric, spin resonance, and luminescence techniques, as well as enzymes which produce such molecules. Among the useful nonradioactive labeling materials are organometallic compounds. Because of the rarity of some metals in biological systems, methods which specifically assay the metal component of the organometallic compounds can be successfully exploited. For example, Cais, U.S. Pat. No. 4,205,952 (1980) discloses the use of immunochemically active materials labels with certain organometallic compounds for use in quantitating specific antigens. Any general method of detecting the chosen metals can be used with these labels, including emission, absorption and fluorescence spectroscopy, atomic absorption, and neutron activation. The methods often suffer from lack of sensitivity, can seldom be adapted to a homogeneous system, and as with atomic absorption, sometimes entail destruction of the sample.

Of particular interest are labels which can be made to luminesce through photochemical, chemical, and electrochemical means. "Photoluminescence" is the process whereby a material is induced to luminesce when it absorbs electromagnetic radiation. Fluorescence and phosphorescence are types of photoluminescence. "Chemiluminescent" processes entail the creation of the luminescent species by a chemical transfer of energy. "Electrochemiluminescence" entails the creation of the luminescent species electrochemically.

These luminescent systems are of increasing importance. For example, Mandle, U.S. Pat. No. 4,372,745 (1983), discloses the use of chemiluminescent labels in immunochemical applications. In the disclosed systems, the labels are excited into a luminescent state by chemical means such as by reaction of the label with $H_2O_2$ and an oxalate. In these systems, $H_2O_2$ oxidatively converts the oxalate into a high energy derivative, which then excites the label. This system will, in principle, work with any luminescent material that is stable in the oxidizing conditions of the assay and can be excited by the high energy oxalate derivative. Unfortunately, this very versatility is the source of a major limitation of the technique: typical biological fluids containing the analyte of interest also contain a large number of potentially luminescent substances that can cause high backround levels of luminescence.

Another example of the immunochemical use of chemiluminescence which suffers from the same disadvantages in Oberhardt et al., U.S. Pat. No. 4,280,815 (1981), who disclose the in situ electrochemical generation of an oxidant (e.g., $H_2O_2$) in close proximity to an immunoreactant labeled with a chemiluminescent species. The electrogenerated oxidant diffuses to the chemiluminescent species and chemically oxides it, resulting in the net transfer of one or more electrons to the electrogenerated oxidant. Upon oxidation, the chemiluminescent species emits a photon. In contrast, the subject invention requires the direct transfer of electrons from a source of electrochemical energy to a chemiluminescent species which is capable of repeatedly emitting photons.

The present invention is concerned with electrochemiluminescent labels. Suitable labels comprise electrochemiluminescent compounds, including organic compounds and organometallic compounds. Electrochemiluminescent methods of determining the presence of labeled material are preferred over other methods for many reasons. They are highly diagnostic of the presence of a particular label, sensitive, nonhazardous, inexpensive, and can be used in a wide variety of applications. Organic compounds which are suitable electrochemical labels include, for example, rubrene and 9,10-diphenyl anthracene. Many organometallic compounds are suitable electrochemical labels, but of particular use are Ru-containing and Os-containing compounds.

Ru-containing and Os-containing organometallic compounds have been discussed in the literature. Cais discloses that any metal element or combination of metal elements, including noble metals from group VIII such as Ru, would be suitable components of organometallic labels detectable by atomic absorption methods. (Cais, col. 11, line 20). However, ruthenium is not a preferred metal in Cais, osmium is not specifically mentioned, no data are presented on the efficiency of using Ru or Os in any of the methods disclosed, and the preferred method of detection, atomic absorption, entails destruction of the Sample.

Weber, U.S. Pat. No. 4,293,310 (1981), discloses the use of Ru-containing and Os-containing complexes as electrochemical labels for analytes in immunoassays. The disclosed complexes are linked to amino groups on the analytes through a linkage. Weber also suggests the possibility of forming carboxylate esters between the labels and hydroxy groups on other analytes.

The presence of the labeled materials can be determined according to Weber, with an apparatus and method which comprises a quencher and an electrochemical flow cell with light means. The photoelectrochemically active label upon photoexcitation transfers an electron to a quencher molecule; the oxidized molecule is subsequently reduced with an electron from an electrode of the flow cell which is held at suitable potential. This electron is measured as photocurrent. The amount of free labeled analyte in the system is determined by the photocurrent signal. This method is the reverse of electrochemiluminescent detection of luminescent materials.

In subsequent reports, Weber et al. discuss the problems associated with the use of this method to detect Ru-containing labels (1). In Table 2 of Weber et al. (1), the extrapolated detection limit for tris(bipyridyl)ruthenium(II) is $1.1 \times 10^{-10}$ moles/L under optimal conditions. In anticipating that the actual use of these labels would entail measurements in the presence of complex mixtures, Weber et al. tested for potential interferents in their system. Table 3 of Weber et al. lists dimethylalkyl amines, EDTA, N-methylmorpholine, N,N'-dimethylpiperazine, hydroxide, oxalate, ascorbate, uric acid, and serum as interferents which would presumably raise the practical detection limit substantially above $1.1 \times 10^{-10}$ moles/L. These studies were performed with a simple Ru-containing compound. No studies were reported in Weber or Weber et al. regarding the limits of detection of complex substances labelled with Ru-containing labels, or on whether the thiourea linkable between the labeled material and label is stable under conditions of the assay.

The particular labels with which the present invention is concerned are electrochemiluminescent. They can often be excited to a luminescent state without their oxidation or reduction by exposing the compounds to electromagnetic radiation or to a chemical energy source such as that created by typical oxalate-$H_2O_2$ systems. In addition, luminescence of these compounds can be induced by electrochemical methods which do entail their oxidation and reduction.

Extensive work has been reported on methods for detecting $Ru(2,2'\text{-bipyridine})_3^{2+}$ using photoluminescent, chemiluminescent and electrochemiluminescent means (2,3). This work demonstrates that bright orange chemiluminescence can be based on the aqueous reaction of chemically generated or electrogenerated $Ru(bpy)_3^{3+}$ (where "bpy" represents a bipyridyl ligand) with strong reductants produced as intermediates in the oxidation of oxalate ions or other organic acids. Luminescence also can be achieved in organic solvent-$H_2O$ solution by the reaction of electrogenerated, or chemically generated $Ru(bpy)_3^{1+}$ with strong oxidants generated during reduction of peroxydisulfate. A third mechanism for production of electrochemiluminescence from $Ru(bpy)_3^{2+}$ involves the oscillation of an electrode potential between a potential sufficiently negative to produce $Ru(bpy)_3^{1+}$ and sufficiently positive to produce $Ru(bpy)_3^{3+}$. These three methods are called, respectively, "oxidative reduction," "reductive oxidation," and "the $Ru(bpy)_3^{3+/+}$ regenerative system."

The oxidative-reduction method can be performed in water, and produces an intense, efficient, stable luminescence, which is relatively insensitive to the presence of oxygen or impurities. This luminescence from $Ru(bpy)_3^{2+}$ depends upon the presence of oxalate or other organic acids such as pyruvate, lactate, malonate, tartrate and citrate, and means of oxidatively producing $Ru(bpy)_3^{3+}$ species. This oxidation can be performed chemically by such strong oxidants as $PbO_2$ or a $Ce(IV)$ salt. It can be performed electrochemically by a sufficiently positive potential applied either continuously or intermittently. Suitable electrodes for the electrochemical oxidation of $Ru(bpy)_3^{2+}$ are, for example, Pt, pyrolytic graphite, and glassy carbon. Although the oxalate or other organic acid is consumed during chemiluminescence, a strong, constant chemiluminescence for many hours can be achieved by the presence of an excess of the consumed material in the reaction chamber.

The reductive-oxidation method can be performed in partially aqueous solutions containing an organic co-solvent such as, for example, acetonitrile. This luminescence depends upon the presence of peroxydisulfate and a means of reductively producing $Ru(bpy)_3^{1+}$ species. The reduction can be performed chemically by strong reductants such as, for example, magnesium or other metals. It can be performed electrochemically by a sufficiently negative potential applied either continuously or intermittently. A suitable electrode for the electrochemical reduction of $Ru(bpy)_3^{2+}$ is, for example, a polished glassy-carbon electrode. As with the oxidative-reduction method, continuous, intense luminescence can be achieved for many hours by inclusion of excess reagents, or by continuous addition of the consumed reagents to the reaction mixture.

The Ru(bpy)$_3^{3+/+}$ regenerative system can be performed in organic solvents such as acetonitrile or in partially aqueous systems, by pulsing an electrode potential between a potential sufficiently negative to reduce Ru(bpy)$_3^{2+}$ and a potential sufficiently positive to oxidize Ru(bpy)$_3^{2+}$. A suitable electrode for such a regenerative system is, for example, a Pt electrode. This system does not consume chemical reagents and can proceed, in principle, for an unlimited duration.

These three methods of producing luminescent Ru-containing compounds have in common the repetitive oxidation-reduction or reduction-oxidation of the Ru-containing compound. The luminescence of solutions containing these compounds is therefore highly dependent on the electric potential of the applied energy source, and is therefore highly diagnostic of the presence of the Ru-containing compound.

Mandle cites Curtis et al. (4) as a possible label in chemiluminescent applications. Curtis et al. reports only unpublished observations that Ru complexes can be induced to emit light when chemically excited by an oxalate/$H_2O_2$ system (Curtis et al., p. 350). Neither Mandle nor Curtis recognized the exceptional utility of ruthenium and osmium complexes in chemiluminescent applications or the utility of electrochemiluminescent systems.

Sprintschnik, G., et al. (5), have described complexes of tris (2,2'-bipyridine)ruthenium(II) esterified with octadecanol or dehydrocholesterol, and have created monolayer films of these surfactant complexes. The complexes were photoluminescent. But when the films were exposed to water, and then to light, the Ru-complexes failed to photoluminesce. This was attributed to photohydrolysis of ester groups in the presence of light.

As described in parent applications Ser. Nos. 858,354 and PCT 87/00987, a variety of analytes of interest and chemical substances that bind to analytes of interest may be conveniently attached to Ru-containing or Os-containing labels through amide or amine linkages. The labeled materials may then be detected by any of a wide variety of means, but by far the most efficient, reliable, and sensitive means are photoluminescent, chemiluminescent, and electrochemiluminescent means. Electrochemiluminescent labels, including Ru-containing and Os-containing labels are particularly versatile and advantageous.

For many years the food industry has been concerned with the presence of biological and chemical contaminants in raw food components and processed foods. While technological advances have been made in reducing the occurrence of food contamination and food borne disease outbreaks resulting therefrom, little progress has been reported in developing rapid and sensitive methods for the detection and identification of food contaminants. Existing standard methods for the detection of harmful contaminants in foods are generally very time consuming, labor intensive, and technically difficult. While the analytical methods themselves for the most part are of adequate sensitivity, the lengthy sample preparation procedures prior to the performance of the detection method often results in low yield of the contaminant in question so that false negatives are frequently encountered.

Two examples which serve to illustrate these problems are the currently recognized standard methods for detecting the presence of Salmonella and Staphylococcal enterotoxins in foods. The detection of Salmonella in food involves several enrichment stages due to the fact that these bacteria, when present in foods, are usually found in low numbers and are often sublethally injured. Therefore, detection methods for Salmonella must be sensitive and allow for the resuscitation and growth of injured cells.

Two methods for Salmonella detection are currently recommended by the U.S. Food and Drug Administration. The methods appear in *The Bacteriological Analytical Manual for Foods*, 6th ed., Association of Official Analytical Chemists, Washington, D.C. (1984). One method is a pure culture technique involving preenrichment, selective enrichment and selective plating, a procedure which requires 4 days to obtain presumptive results and 5 to 7 days to obtain complete results. The other method involves immunofluorescence after selective enrichment. This procedure is more rapid, however it can results in a high incidence of false positive results due to problems of cross reactivity of the polyvalent antisera used in the test (6, 7).

The procedure recommended by the U.S. Food and Drug Administration for the detection of Staphylococcal enterotoxins in foods also appears in *The Bacteriological Analytical Manual for Foods*, 6th ed., Association of Official Analytical Chemists, Washington, D.C. (1984). This method involves the concentration of an extract of a large food sample, e.g., approximately 100 grams, to a small volume, e.g., approximately 0.2 ml, by several dialysis concentration steps and an ion exchange column purification of the sample extract in order to prepare the sample for the microslide double-immunodiffusion technique. This procedure generally requires more than a week to perform.

Tests which are more rapid have recently been developed for the detection of a variety of contaminants such as bacteria, toxins, antibiotics and pesticide residues in foods. In many cases however, sample preparation prior to running the assay continues to be laborious and time consuming. Radioimmunoassays (RIA) and enzyme-linked immunosorbent assays (ELISA) have shortened the hands-on time for the analytical method itself, however these methods are still labor intensive and far from simple to perform. In addition, these methods are usually based on the use of polyclonal antisera, which are variable to specificity and sensitivity, and are generally in short supply for testing for a given food contaminant. ELISA methods have been developed for the analysis of food samples which employ monoclonal antibodies rather than polyclonal antisera. The use of monoclonal antibodies in an assay system for a food contaminant assures the constant supply of reagent which imparts unchanging specificity and sensitivity to the test itself. Monoclonal antibodies have been used in ELISA systems to test for food contaminants such as Salmonella (8) and Staphylococcal enterotoxins (9). Commercially available products for Salmonella detection which employ EIA methodology (Bio-Enzabead Screen Kit, Litton Bionetics) and DNA probe technology (Gene-Trak, Integrated Genetics) are time consuming and labor intensive. Commercially available tests for detection of Staphylococcal enterotoxin in foods which employ reversed passive latex agglutination (SET-EIA, Dr. W. Seiken Co.) and EIA methodology (SET-RPLA, Denka Seiken Co.) and EIA methodology (SER-EIA, Dr. W. Bommeli Laboratories) suffer from the same limitations.

For the past 100 years the bacterium *Escherichia coli* and the coliform group have been commonly used as indicators to monitor water quality and incidences of sewage contamination.

Current detection methodologies for *E. coli* and/or coliforms are based on the properties of acid or gas production from the fermentation of lactose. The most widely used methods are: the Most Probable Number (MPN) assay and the Membrane Filtration (MF) test. Both techniques are approved by the Environmental Protection Agency (EPA) and the American Public Health Association (APHA) for the microbiological examination of water and waste water (10), and also by the Food and Drug Administration (FDA) for the bacteriological examination of milk and foods (11).

The MPN method is actually comprises of three (12) separate assays (10). In the Presumptive test, a nonselective medium such as Lauryl Sulfate Tryptose (LST) broth or Lactose broth is used to check for gas production from the fermentation of lactose. Gas positive tubes are then subcultured into a more selective medium, Brilliant Green Lactose Bile (BGLB) broth for coliforms and E. coli (EC) broth for fecal coliforms, and again checked for gas production (confirmed test). Samples from positive Confirmatory tests are required to be tested further by plating on a selective and differential medium like Eosin Methylene Blue (EMB) agar or Endos agar, followed by Gram Stain and some biochemical tests to firmly establish the presence of the indicator bacteria (Completed test). The entire MPN assay may require up to five (5) days for completion; therefore, for routine water analysis, most laboratories use only the Presumptive and the Confirmed portions of the MPN assay, which still requires 48 hours to 72 hours to complete. In addition to being time consuming and cost ineffective in terms of materials, incidences of both false positive and false negative reactions have also been commonly encountered in the MPN assays (15, 16, 20).

The MF technique for the bacteriological examination of water was introduced in the early 1950's (12). Unlike the MPN assay, which was tedious and time consuming, MF analysis could be complete in 24 hours without the need for further confirmations. The basic MF procedure is as follows: A volume of water sample, usually 100 ml is filtered through a 0.45 um pore diameter filter, and then incubated on a sterile pad saturated with selective medium. The two media most often used are the mEndo broth, selective for coliforms at 35° C., and the mFC broth, selective for fecal coliforms at 44.5° C. (10). Since the introduction of the media, numerous authors have reported that both the mEndo and the mFC broth tends to underestimate the actual numbers of indicator bacterial present, due either to the selectivity of the medium or the high temperature used for incubation (44.5° C.) (21, 22). Such incidences of false negatives have been especially prevalent when the organisms in the sample have been sublethally injured by environmental factors and/or chemicals (17, 18). Recently, modifications have been proposed by the EPA to follow up the MF test by a confirmatory procedure, whereby at least ten colonies on each filter need to be checked for gas production using the LST broth followed by BGLB broth as in the MPN assay (14). Such modifications although would reduce the incidences of both false negative and false positive reactions, it would also increase material cost as well as triple the MF assay time from 24 hours to 72 hours.

In 1982, Feng and Hartman introduced a fluorogenic assay for the detection of E. coli using the substrate 4-methyl umbelliferone glucuronide (MUG) (13). E. coli cells produced the enzyme beta-glucuronidase which would cleave the substrate releasing the fluorogenic 4-methylumbelliferone radical (19). By incorporating the compound MUG into the Presumptive LST medium, a single tube of LST-MUG medium provided both the Presumptive data (gas production) and the Confirmed data (fluorescence) for fecal coliforms within 24 hours. Although the MUG assay was rapid and simple, only 85% to 95% of the E. coli (depending on source) produced this enzyme, hence the test was not 100% reliable. Also the system was not applicable to the coliform group.

Currently, no suitable assay exists for the detection and enumeration of coliforms and fecal coliforms in a sample. The development of a simple, rapid, and reliable detection assay would not only decrease cost and time, but also greatly increase the efficiency of monitoring water sanitation and food processing and handling.

SUMMARY OF THE INVENTION

The invention is in a chemical moiety having the formula $$[Re(P)_m(L^1)_n(L^2)_o(L^3)_p(L^4)_q(L^5)_r(L^6)_s]_t(B)_u \qquad (I),$$

wherein P is a polydentate ligand of Re; $L^1$, $L^2$, $L^3$, $L^4$, $L^5$, and $L^6$ are ligands of Re, each of which may be the same as, or different from, each other ligand; B is a substance which is a ligand of Re or is conjugated to one or more of P, $L^1$, $L^2$, $L^3$, $L^4$, $L^5$, $L^6$; m is an integer equal to or greater than 1; each of n, o, p, q, r, and s is zero or an integer; t is an integer equal to or greater than 1; u is an integer equal to or greater than 1; and P, $L^1$, $L^2$, $L^3$, $L^4$, $L^5$, $L^6$, and B are of such composition and number that the chemical moiety can be induced to emit electromagnetic radiation and the total number of bonds to Re provided by the ligands of Re equals the coordination number of Re.

Particularly preferred embodiments of this chemical moiety comprise

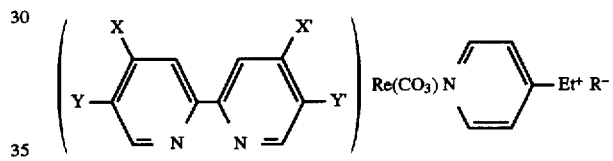

wherein X and X' and Y and Y' may be the same or different, X and X' may be $N(CH_2H_5)_2$, $CH_3$, $CH_3O$, $C_6H_5$, Cl, $CO_2CH_3$, CN, or $NO_2$, and Y and Y' may be either H or $CH_3$, provided that if X and X' and Y and Y' are the same and X is $CO_2CH_3$, Y is not H and further provided that if X and X' and Y and Y' are the same, X and Y are not H; and R is an anion.

A first major advantage of the electrochemiluminescent chemical moieties containing the metal rhenium is in the ease of preparation of those moieties. Both bipyridyl and nonbipyridyl derivatives can be used in the synthesis of the moieties and in the ultimate function of those moieties in conjugating an analyte of interest.

A further important advantage offered by the Re(I) complexes versus the analogous Ru(II) complexes is that they permit, by choice of one or more substituents on the ligands bound to Re, tuning of the emission wavelength (i.e., color) for the Re(I) complexes over most of the visible spectral region (i.e., 500 nm–800 nm). The origins of this property lie in the quantum mechanical properties of the complexes. The quantum efficiencies of these complexes are also superior to those of Ru(II).

The Re complexes are used in a method for detecting the presence of a chemical moiety having formula I. The method broadly comprises: (a) forming a reagent mixture under suitable conditions containing the Re-containing chemical moiety; (b) inducing the moiety to emit electromagnetic radiation by exposing the reagent mixture to chemical energy, electrochemical energy, or electromagnetic energy; and (c) detecting the emitted electromagnetic radiation and thereby determining the presence of the chemical moiety.

These methods of this invention include detecting the chemical moiety where the moiety is capable of binding to a chemical agent, i.e., forming a specific complex with a chemical agent.

Methods for determining the presence of analytes of interest which bind to a chemical moiety having formula I are also described as are methods of determining the presence of an analyte of interest wherein the analyte and a chemical moiety bind competitively to a complementary material.

The invention is also in a method of detecting in a predetermined volume of a multicomponent, liquid sample either the presence of or the amount of an analyte of interest which comprises: (a) contacting a sample with a reagent comprising an electrochemiluminescent chemical moiety containing a rhenium-containing compound wherein said compound is (i) capable of being induced to repeatedly emit electromagnetic radiation upon exposure to an amount of chemical, electrochemical, or electromagnetic energy from a suitable source effective to induce the reagent to repeatedly emit radiation and (ii) capable of combining with the analyte of interest, the contact being effected under appropriate conditions such that the analyte and the reagent combine; (b) exposing the resulting sample to an amount of chemical, electrochemical, or electromagnetic energy from a suitable source effective to induce the reagent to repeatedly emit radiation, the exposure being effected under suitable conditions so as to induce the reagent to repeatedly emit electromagnetic radiation; and (c) detecting or quantitatively measuring the amount of electromagnetic radiation so emitted and thereby detecting or quantifying the presence of the analyte of interest in the sample.

The invention is also in a competitive method for detecting in a predetermined volume of a multicomponent, liquid sample either the presence of or the amount of an analyte of interest present in the sample which comprises: (a) contacting the sample with a reagent comprising an electrochemiluminescent chemical moiety containing a rhenium-containing compound wherein said compound is (i) capable of being induced to repeatedly emit electromagnetic radiation upon exposure to an amount of chemical, electrochemical, or electromagnetic energy from a suitable source effective to induce the reagent to repeatedly emit radiation and (ii) capable of competing with the analyte of interest for binding sites on a complementary material not normally present in the sample, and with the complementary material, the contact being effected under appropriate conditions such that the analyte of interest and the reagent competitively bind to the complementary material; (b) exposing the resulting sample to an amount of electrochemical energy from a suitable source effected to induce the reagent to repeatedly emit radiation, the exposure being effective under suitable conditions so as to induce the reagent to repeatedly emit electromagnetic radiation; and (c) detecting or quantitatively measuring the amount of electromagnetic radiation so emitted and thereby detecting or quantifying the presence of the analyte of interest in the sample.

The invention also is in methods for detecting and identifying the presence or the amount of a multiplicity of analytes of interest in a liquid food or food homogenate. This method comprises: (a) immersing into the liquid food or food homogenate a portion of a diagnostic reagent holder suitable for immersing into a liquid or solid suspension and having immobilized to it a multiplicity of reagents, each reagent being immobilized to the diagnostic reagent holder in distinct, identifiable regions and capable of forming a complex with a single analyte of interest so as to allow the formation of immobilized reagent-analyte of interest complexes; (b) removing the diagnostic reagent holder from the liquid food or food homogenate; (c) rinsing the diagnostic reagent holder with a suitable rinsing solution; (d) immersing the portion of the diagnostic reagent holder which contains the immobilized reagent-analyte of interest complexes into a detection solution which contains at least one detection reagent capable of forming complexes with the immobilized reagent-analyte of interest complexes so as to allow the formation of immobilized reagent-analyte of interest detection reagent complexes; (e) detecting the presence on the identifiable regions of the diagnostic reagent holder to which reagents are immobilized reagent-analyte of interest-detection reagent complexes, thereby detecting and identifying the presence or the amount of a multiplicity of analytes of interest in the liquid food or food homogenate.

DESCRIPTION OF THE DRAWINGS

FIG. 2 is a calibration graph showing the effect of the concentration of a rhenium-containing calibrant upon the electrochemiluminescent intensity of an osmium-containing internal standard;

FIG. 3 is a curve showing the effect of an osmium-containing internal standard upon the electrochemiluminescence of a rhenium-containing calibrant.

DETAILED DESCRIPTION OF THE INVENTION

New Chemical Moieties Containing Re

Figure 1:
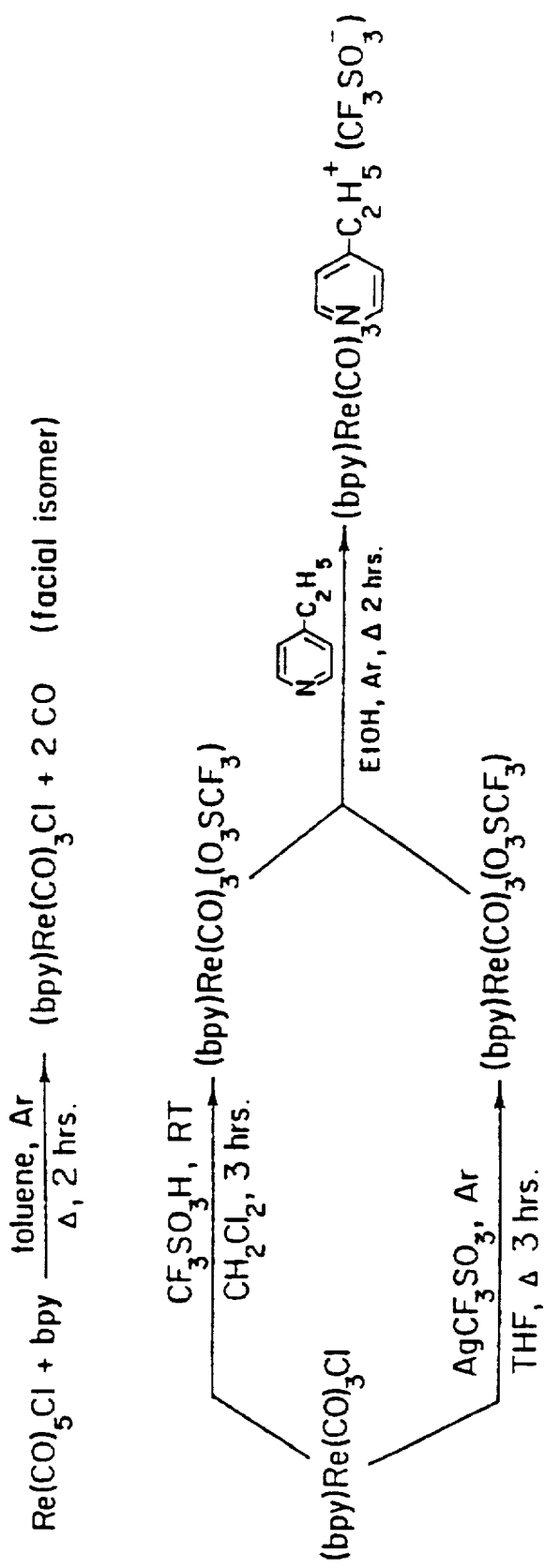
FIG. 1 is a schematic representation of methods for preparing the Re-containing moieties of the invention.

The invention is in a chemical moiety having the formula

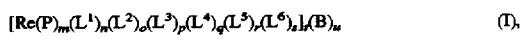

wherein P is a polydentate ligand of Re; $L^1$, $L^2$, $L^3$, $L^4$, $L^5$, and $L^6$ are ligands of Re, each of which may be the same as, or different from, each other ligand; B is a substance which is a ligand of Re or is conjugated to one or more of P, $L^1$, $L^2$, $L^3$, $L^4$, $L^5$, or $L^6$; m is an integer equal to or greater than 1; each of n, o, p, q, r, and s is zero or an integer; t is an integer equal to or greater than 1; u is an integer equal to or greater than 1; and P, $L^1$, $L^2$, $L^3$, $L^4$, $L^5$, $L^6$, and B are of such composition and number that the chemical moiety can be induced to emit electromagnetic radiation and the total number of bonds to Re provided by the ligands of Re equals the coordination number of Re.

This chemical moiety must have at least one polydentate ligand of Re. If the moiety has more than one polydentate ligand, the polydentate ligands may be the same or different. Polydentate ligands include aromatic and aliphatic ligands. Suitable aromatic polydentate ligands include aromatic heterocyclic ligands. Preferred aromatic heterocyclic ligands are nitrogen-containing, such as, for example, bipyridyl, bipyrazyl, terpyridyl, phenanthroyl and porphyrins.

Suitable polydentate ligands may be unsubstituted, or substituted by any of a large number of substituents known to the art. Suitable substituents include, for example, alkyl, substituted alkyl, aryl, substituted aryl, aralkyl, substituted aralkyl, carboxylate, carboxaldehyde carboxamide, cyano, amino, hydroxy, imino, hydroxycarbonyl, aminocarbonyl, amidine, guanidium, ureide, maleimide sulfur-containing groups, phosphorus-containing groups, and the carboxylate ester of N-hydroxysuccinimide.

Additionally, at least one of $L^1$, $L^2$, $L^3$, $L^4$, $L^5$, and $L^6$ may be a polydentate aromatic heterocyclic ligand. Furthermore, at least one of these polydentate aromatic heterocyclic ligands may contain nitrogen. Suitable polydentate ligands include, but are not limited to, bipyridyl, bipyrazyl, terpyridyl, phenanthroyl, a porphyrin, substituted bipyridyl, substituted bipyrazyl, substituted terpyridyl, substituted phenanthroyl or a substituted porphyrin. These substituted polydentate ligands may be substituted with an alkyl, substituted alkyl, aryl, substituted aryl, aralkyl, substituted aralkyl, carboxylate, carboxaldehyde, carboxamide, cyano, amino, hydroxy, imino, hydroxycarbonyl, aminocarbonyl, amidine, guanidium, ureide, maleimide, a sulfur-containing group, a phosphorus-containing group, or the carboxylate ester of N-hydroxysuccinimide.

In one embodiment of the invention, the chemical moiety contains two bidentate ligands, each of which is bipyridyl, bipyrazyl, terpyridyl, phenanthroyl, substituted bipyridyl, substituted bipyrazyl, substituted terpyridyl, or substituted phenanthroyl.

In another embodiment of the invention, the chemical moiety contains three bidentate ligands, each of which is bipyridyl, bipyrazyl, terpyridyl, phenanthroyl, substituted bipyridyl, substituted bipyrazyl, substituted terpyridyl, or substituted phenanthroyl. In yet another embodiment of the invention, two bidentate bipyridyl ligands, and one substituted bidentate bipyridyl ligand may be used.

In still another embodiment of the invention, the chemical moiety contains a tetradentate ligand such as a porphyrin or substituted porphyrin.

This chemical moiety may have one or more monodentate ligands, a wide variety of which are known to the art. Suitable monodentate ligands include, for example, carbon monoxide, cyanides, isocyanides, halides, and aliphatic, aromatic, and heterocyclic phosphines, amines, stibines, and arsines.

Suitable ligands include a compound having the structure

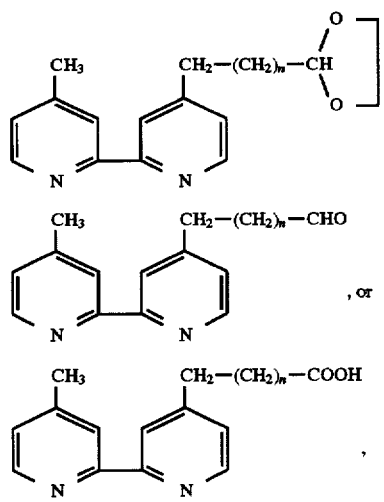

wherein n is an integer. In a preferred embodiment, n is 2.

Another suitable ligand is a compound having the structure

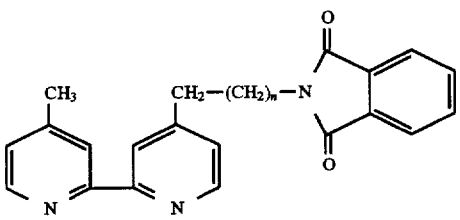

wherein n is an integer. In a preferred embodiment, n is 3.

Another ligand is a compound having the structure

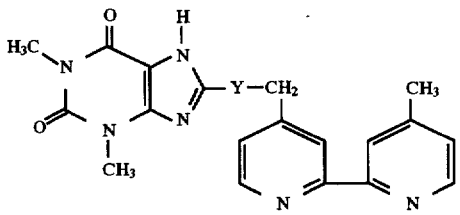

wherein Y is a linker arm. In one embodiment, Y has the structure

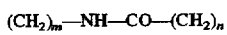

$(CH_2)_m-NH-CO-(CH_2)_n$ wherein m an n are integers, which may be the same or different, greater than or equal to 1. In one embodiment of the invention, m is 3 and n is 2.

Yet another ligand is a compound having the structure

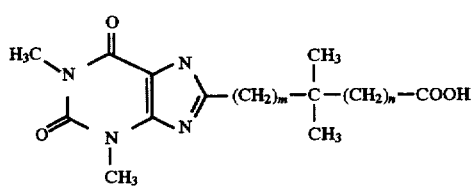

wherein m an n are integers which may be the same of different. In one embodiment of the invention, m and n are both 1.

Preferred Rhenium-Containing Moieties

Preferred rhenium-containing moieties of the invention have the formula

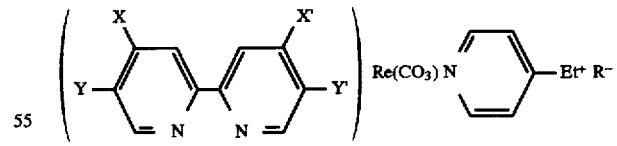

wherein X and X' and Y and Y' may be the same or different, X and X' may be $N(CH_2H_5)_2$, $CH_3$, $CH_3O$, $C_6H_5$, Cl, $CO_2CH_3$, CN, or $NO_2$, and Y and Y' may be either H or $CH_3$, provided that if X and X' and Y and Y' are the same and X is $CO_2CH_3$, Y is not H and further provided that if X and X' and Y and Y' are the same, X and Y are not H; and R is an anion. Compounds which may advantageously be used are those wherein X and Y are as identified in Table 1 below. The method of preparation, yield and λ ($CH_3CN$) are also indicated.

TABLE 1

| X | Y | Method | Yield (%) | λ(CH₃CN)ᵉᵐ |
|---|---|---|---|---|
| N(C₂H₅)₂ | H | acid | 58 | 509 nm |
| CH₃ | CH₃ | silver | 33 | 526 |
| CH₃ | H | silver | 80 | 526 |
| H | H | acid | 9.0 | 567 |
| CH₃ | H | silver | 74 | 569 |
| Ph | H | acid | 25 | 579 |
| Cl | H | silver | 24 | 603 |
| CO₂CH₃ | H | silver | 18 | 625 |
| CN | H | | | |
| NO₂ | H | acid | 56 | 675 |

Spectroscopic data are provided in the following table.

| | Spectroscopic Characterization | | | | | |
|---|---|---|---|---|---|---|
| | CH₃CN | | | Water | | |
| Compound | Emission max (nm) | Φr | t | Emission (nm) | (degassed) | Air saturated |
| A (NEt)₂ | 528 | 0.1102 | 80 (dg) 3398 | 530 | 4923 | 711 |
| B (Me)₄ | 565 | 0.0907 | 190 (dg) 1500 | 545 | 806 | 656 |
| C (OCH₃)₂ | 584 | 0.0195 | 71 (dg) 155 | 590 | 93 | 66 |
| D³ (Me)₂ | 582 | 0.0352 | 109 (dg) 282 | 575 | 142 | 140 |
| E (O)₂ | 602 | 0.0566 | 184 (dg) 351 | 590 | 143 | 140 |
| F³ (Cl)₂ | 636 | 0.0064 | 31 (dg) 36 | 625 | 25 | 23 |
| G (CO₂Me)₂ | 660 | 0.0122 | 61 (dg) 75 | 640 | 74 | 40 | dg - degassed, or quantum yield, fluorescence lifetime in n sec.
[1]Excitation at 355
[2]N₂ gas laser excitation 337
[3]These compounds were found to be stable after heating at 65° for 15 minutes in 10× sequencing buffer (0.1M Tris-HCl buffered at pH 7.5, 0.1M MgCl₂, 0.5M NaCl) diluted 8 times with deionized water. Other compounds were not tested but are expected to behave similarly.

Suitable compounds of the invention have the following structure

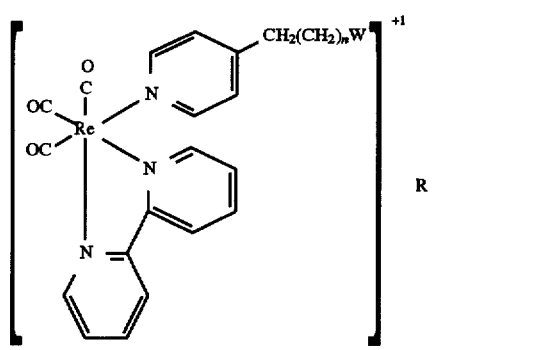

wherein n is an integer, preferably 2 or 3, W is CHO, COOH, NH₂ or Br, and R is an anion. The bipyridyl group may be unsubstituted or substituted as described above.

One compound may be

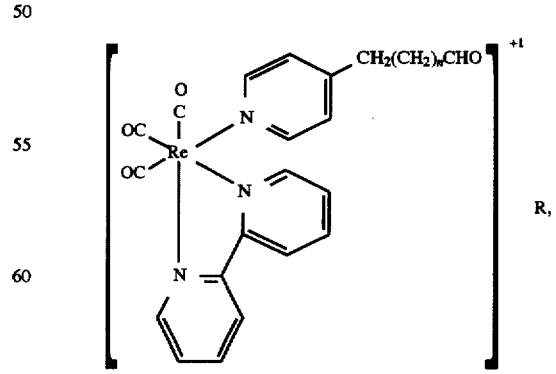

wherein R is an anion and n is preferably 2 or 3.

Another compound may be

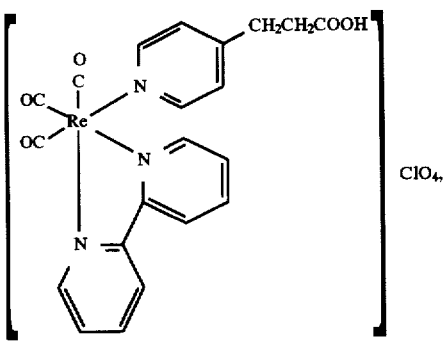

where n is 2 or 3.

Another compound may be

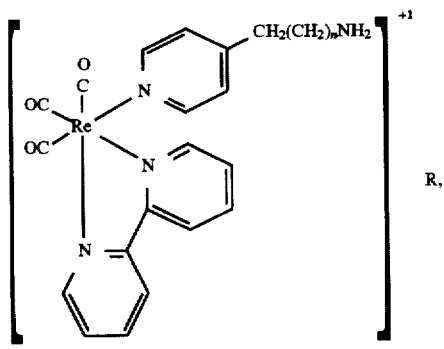

where n may be 2 or 3.

Another compound may be

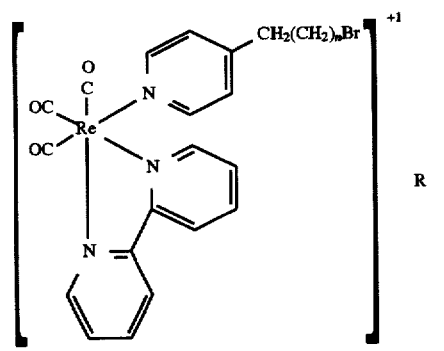

where n may be 2 or 3.

These compounds may comprise a composition of matter having the structure

X—(Y)$_n$—Z wherein X represents one or more necleotides which may be the same or different, one or more amino acids which may be the same or different, an antibody, an analyte of interest or an analogue of an analyte of interest, n represents an integer, and Z represents the compound provided by this invention. X may be, e.g., theophylline, digoxigenin, or a peptide derived from hCG.

Also provided by the invention is a composition of matter having the structure

X—CH=CH—CO—NH—(CH$_2$)$_n$—NH—CO—(CH$_2$)$_m$—Z wherein:

X represents one or more nucleotides which may be the same or different;

Z represents an electrochemiluminescent chemical moiety;

n represents an integer greater than or equal to 1; and m represents an integer greater than or equal to 1.

In one embodiment of the invention, Z is bis(2,2'-bipyridine) [4-(butan-1-al)-4' methyl-2,2'bipyridiine] rhenium.

In yet another embodiment of the invention, the thymidine nucleotide is a 3' terminal nucleotide attached to the nucleotide sequence

TCACCAATAAACOGCAAACACCATCCOGTCCTGCCAG

Also provided is a composition of matter having the structure

[T—Y—Z]$^{1+}$(R)

wherein T represents theophylline, Y represents a linker group attching to to Z, Z represents bis-(2,2'-bipyridine) [4-methyl-2,2'-bipyridine-4'-yl] (I) and R represents an anion.

In one embodiment of the invention, Y is attached to the carbon at position 8 of T. In another embodiment of the invention, Y has the structure (CH$_2$)$_m$—CO—NH—(CH$_2$)$_n$ wherein m an n represent an integer, which may be the same or different, greater than or equal to 1. In another embodiment of the invention, m is 3 and n is 4. In another embodiment of the invention, m and n are both 3.

In yet another embodiment of the invention, Y has the structure $$(CH_2)_m-\underset{\underset{CH_3}{|}}{\overset{\overset{CH_3}{|}}{C}}-(CH_2)_n-CO-NH-CH_2)_r$$

wherein m, n, an r represent an integer, which may be the same or different, greater than or equal to 1. In one embodiment of the invention, m is 1, n is 1, and r is 4.

In yet another embodiment of the invention, Y is attached to the nitrogen at position 7 of T. In one embodiment of the invention, Y has the structure (CH$_2$)$_n$ wherein n is an integer greater than or equal to 1. In still another embodiment of the invention, n is 4.

Also included in the invention is a composition of matter having the structure

X—Z wherein X represents one or more amino acids which may be the same or different, comprising at least one amino acid which is cysteine or methionine, and Z is bis (2,2'-bipyridine) maleimidohexanoic acid, 4-methyl-2, 2'bipyridine-4'-butylamide rhenium attached by the carbon at position 3 or 4 of the maleimide to a sulfur substituent of cysteine or methionine.

It is within the scope of the invention for one or more of the ligands of Re to be attached to additional chemical labels, such as, for example, radioactive isotopes, fluorescent components, or additional luminescent ruthenium-containing or osmium-containing centers.

It is also within the scope of this invention for the labeled substance (B) to be labeled by more than one, e.g., two, three, four, or more electrochemiluminescent centers.

Suitable substances (B) include many biological substances, for example, whole cells, viruses, subcellular particles, proteins, lipoproteins, glycoproteins, peptides, nucleic acids, polysaccharides, lipopolysaccharides, pharmacological agents, tranquilizers, barbiturates, alkaloids, steroids, vitamins, amino acids, and sugars. Whole cell may be animal, plant, or bacterial, and may be viable or dead. Examples include plant pathogens such as fungi and nematodes. Within this application, the term "subcellular particles" means subcellular organelles, membrane particles as from disrupted cells, fragments of cell walls, ribosomes, multienzyme complexes, and other particles which can be derived from living organisms. Also, within this application, "nucleic acids" means chromosomal DNA, plasmid DNA, viral DNA, and recombinant DNA derived from multiple sources. Nucleic acids also include RNAs, for example, messenger RNAs, ribosomal RNAs and transfer RNAs. Polypeptides include, for example, enzymes, transport proteins, receptor proteins, and structural proteins such as viral coat proteins. Preferred polypeptides are enzymes and serum-derived antibodies. Particularly preferred polypeptides are monoclonal antibodies. Hormones include, for example, insulin and T4 thyroid hormone. Pharmacological agents include, for example, cardiac glycosides. It is also within the scope of this invention to include synthetic substances which chemically resemble biological materials, such as synthetic peptides, synthetic nucleic acids, and synthetic membranes, vesicles, and liposomes. The foregoing is not intended to be a comprehensive list of the biological substances suitable for use in this invention, but is meant only to illustrate the wide scope of the invention.

It is within the scope of this invention to include labeled nonbiological substances, including polymeric materials. These substances may be in the form of soluble polymeric molecules, or any of the large variety of known macroscopic forms such as, for example, beads, or containers such as test tubes, bottles, assay wells, or the like.

Biological and nonbiological substances (B) may be conjugated to a ligand of Re where such conjugation is by way of amide or amine linkages. The linkages may be oriented so that material (B) is bonded directly either to the carbonyl or to the nitrogen of the amide linkage. These chemical moieties may be ionized. If so, it is understood in the art that many different counterions will serve to neutralize the charge of preparations of the chemical moiety. Suitable cations include, for example $H^+$, $NH_4^+$, guanidium, $Ag^+$, $Li^+$, $Na^+$, $K^+$, $Mg^{2+}$, $Mn^{2+}$, and $Cd^{2+}$. Suitable anions include, for example, halides, $OH^-$, carbonate, $SO_4^{2-}$, hexafluorophosphate, and tetrafluoroborate.

Advantages of Re-Containing Moieties

A major advantage of the electrochemiluminescent chemical moieties containing the metal rhenium is in the ease of preparation of those moieties. Both bipyridyl and nonbipyridyl derivatives can be used in the synthesis of the moieties and in the ultimate function of those moieties in conjugating an analyte of interest.

The rhenium moieties can be synthesized in two-step processes in contrast to the osmium and ruthenium complexes which require 3, 4 or 5 steps. FIG. 1 describes, schematically, the two process steps employed to prepare the rhenium containing moieties of the invention.

With reference to FIG. 1, the starting material for the preparation of the luminescent Re(I) complexes is $Re(CO)_5Cl$. The synthesis of the desired Re(I) species involves two steps. In the first step, substitution of CO by chelating 2,2'-bipyridine ligand produces the facial isomer, fac-(L)Re$(CO)_3Cl$. L is a chelating 2,2'-bipyridine ligand, e.g., bpy, $Cl_2$bpy, $(CO_2CH_3)_2$bpy, $(NO_2)_2$bpy, $Me_2$bpy, $Ph_2$bpy, $(CH_3O)_2$bpy, $Me_4$bpy, or $(NEt_2)_2$bpy.

The conversion of fac-(L)Re$(CO)_3$ to the corresponding fac-(L)Re$(CO)_3$(Etpy)(RK (where R is $CF_3CO_3^-$, $PF_6^-$, $Clo_4^-$) is accomplished by either an acid method or a silver method.

The acid method is useful for bipyridyl ligands that are insensitive, i.e., stable, to strongly acidic media. It involves the production and isolation of the intermediate Re(I) triflate species followed by conversion to the 4-pyridyl ethane derivative.

The silver method is used for complexes containing bipyridyl ligands susceptible to decomposition in highly acidic environments, e.g.,L=$(CH_3O)_2$bpy or $(COOCH_3)_2$bpy. In this method, a soluble silver trifluoromethane sulfonate salt is reacted with the fac-(L)Re$(CO)_3Cl$ species to form the fac-(L)Re$(CO)_3(O_3SCF_3)$ moiety and insoluble AgCl. After removal of the AgCl precipitate by filtration, the solution is reacted in situ with 4-pyridyl ethane to produce the desired product.

Another important advantage offered by the Re(I) complexes described herein versus the analogous Ru(II) complexes relates to their ability to permit tuning of the emission wavelength (i.e., color) for the Re(I) complexes over most of the visible spectral region (i.e., 500 nm–800 nm). The origins of this property lie in the quantum mechanical characteristics of the light emission process for the complexes.

A quantum mechanical analysis of the luminescence process for Ru(II) complexes indicates that (1) with few exceptions, the observation of room temperature luminescence in fluid solution requires coordination of 3 chelating ligands of the bipyridyl or phenanthroyl type to the Ru(II); (2) quantum states existing at energies near the emissive state limit the luminescence intensity available from Ru(II) complexes; (3) substitution of groups on the chelating bipyridyl or phenanthroyl ligands results in only limited changes in the emission energies of the Ru(II) complexes; and (4) the luminescence efficiency generally decreases as the maximum emission wavelength increases for the Ru(II) complexes. These factors limit the usable wavelength range to 580 nm to 750 nm at room temperature in fluid solution.

A similar analysis of the emission process for rhenium complexes indicates that (1) emission in room temperature fluid solution requires that only one coordinating bipyridyl or phenanthroyl ligand be present at the Re(I) center. Although 3 CO ligands are also required, there is considerable leeway in the choice of the final monodentate coordinating ligand (e.g., Cl, pyridine, $CH_3CN$, etc.). The emission wavelength maximum is controlled by the identity of this monodentate ligand and the substitution pattern at the chelating bipyridyl or phenanthroyl moiety. This leads in part to the wider range of emission wavelengths available for these complexes versus the Ru(II) species.

There are no quantum states with energies near the emissive state that can inhibit emission in the Re(I) complexes. In contrast, in the Ru(II) complexes, the emission efficiency generally falls as the wavelength of the emission maximum increases.

Thus, the usable wavelength range of emission for the Re(I) complexes is approximately 500 nm–800 nm. The slight increase in the red response for the Re(I) versus Ru(II) complexes is due primarily to the somewhat increased broadness of the Re(I) emission spectra versus the Ru(II) emission spectra.

The Re(I) complexes thus have an increased range of accessible emission wavelengths as compared with the Ru(II) compounds. The unique structure of the Re(I) complexes also permits greater flexibility and ease in selecting the desired maximum emission wavelength by structural modification of the complex than is possible with the Ru(II) complexes. The greater range of available emission wavelengths for Re(I) versus Ru(II) allows one to measure emission from one Re(I) complex in a solution of several luminescing Re(I) species with minimal interference from and error due to the competing Re(I) luminescers.

Improved Assays Using Re-Containing Moieties

The invention is also in methods of determining the presence of a chemical moiety having formula I. The method comprises: (a) forming a reagent mixture under suitable conditions containing the Re-containing chemical moiety; (b) inducing the moiety to emit electromagnetic radiation by exposing the reagent mixture to chemical, electrochemical, or electromagnetic energy; and (c) detecting the emitted electromagnetic radiation and thereby determining the presence of the chemical moiety.

Suitable conditions for forming the reagent mixture will be known to those skilled in the art and will depend on the type of reagent mixture involved. For example, suitable conditions for an aqueous reagent mixture may include appropriate concentrations of chemical moiety and other reagents such as oxidants, pH, salt concentration and the like. For a solid sample, suitable conditions for forming a reagent mixture may include addition of a conducting liquid.

The methods of this invention include methods of detecting the chemical moiety wherein the moiety is capable of binding to a chemical agent, i.e., forming a specific complex with the chemical agent. Suitable agents include, but are not limited to, whole cells, viruses, subcellular particles, nucleic acids, polysaccharides, proteins, glycoproteins, lipoproteins, lipopolysaccharides, lipids, fatty acids, peptides, cellular metabolites, hormones, pharmacological agents, tranquilizers, barbiturates, alkaloids, steroids, vitamins, amino acids, sugars, or nonbiological polymers. In one embodiment of the invention, the chemical agent may be immobilized on the surface of an assay vessel. In another embodiment, the chemical agent may be a serum-derived antibody or a monoclonal antibody. Of particular interest are antibody-antigen pairs of materials. This binding method may be used to determine the presence of labeled antigens, such as, for example, digoxin or digitoxin in complex mixtures such as blood, urine, or synthetic reaction mixtures by first exposing the mixture to immobilized antibodies specific for the antigen of interest, and then measuring the amount of labeled material bound to the immobilized antibodies.

The invention also includes methods for determining the presence of analytes of interest which bind to a chemical moiety having the formula I. The method comprises: (a) forming a reagent mixture under suitable conditions containing the Re-containing chemical moiety; (b) inducing the moiety to emit electromagnetic radiation by exposing the reagent mixture to chemical, electrochemical, or electromagnetic energy; and (c) detecting the emitted electromagnetic radiation and thereby determining the presence of the analyte of interest.

Also provided are methods of determining the presence of an analyte of interest wherein the analyte and a chemical moiety having formula I bind competitively to a complementary material. By "complementary material" is meant any substance capable of forming complexes with both an analyte of interest and a labeled analyte of interest or a labeled analogue of an analyte of interest. The method comprises: (a) contacting the complementary material, the Re-containing chemical moiety, and the analyte under suitable conditions so as to form a reagent mixture; (b) inducing the chemical moiety to emit electromagnetic radiation by exposing the reagent mixture to chemical, electrochemical, or electromagnetic energy; and (c) detecting the emitted electromagnetic radiation and thereby determining the analyte of interest.

The phrase, "inducing to emit electromagnetic radiation," refers to creating an excited state of moiety which luminesces at wavelengths between 200 nanometers (nm) and 900 nanometers (nm) at ambient temperatures. Variations in the chemical structure of the ligands can change the value of the energy input required to create the luminescent excited state. Similarly, the wavelength of the emitted electromagnetic radiation is dependent upon the nature and environment of the rhenium-containing material.

Generally, photoluminescence excitation and emission occur with electromagnetic radiation of between about 200 nanometers and about 900 nanometers in wavelength. Likewise, chemiluminescent and electrochemiluminescent emission generally occur with the emitted electromagnetic radiation being between about 200 nanometers and about 900 nanometers in wavelength. The potential at which the reduction or oxidation of the chemical moiety occurs depends upon its exact chemical structure as well as factors such as the pH of the solution and the nature of the electrode used. It is well known how to determine the optimal emission and excitation wavelengths in a photoluminescent system and the optimal potential and emission wavelength of an electrochemiluminescent and chemiluminescent system.

There are many methods for quantifying the amount of luminescent species present. The rate of energy input into the system can provide a measure of the luminescent species. Suitable measurements include, for example, measurements of electric current when the luminescent species is generated electrochemically, the rate of reductant or oxidant utilization when the luminescent species is generated chemically or the absorption of electromagnetic energy in photoluminescent techniques. In addition, the luminescent species can be detected by measuring the emitted electromagnetic radiation. All of these measurements can be made either as continuous, rate-based measurements, or as cumulative methods which add the signal over a long period of time. Rate-based measurements may be carried out with photomultiplier tubes, photodiodes or phototransistors to produce electric currents proportional in magnitude to the incident light intensity, or by using charge couple devices. Examples of cumulative methods are the integration of rate-based data, and the use of photographic film to provide cumulative data directly.

All of these luminescence-based methods entail repeated luminescence by the rhenium-containing compound. The repetitive nature of the detectable event distinguishes these labels from radioactive isotopes or bound chemiluminescent molecules such as luminol. The latter labels produce a detectable event only once per molecule (or atom) of label, thereby limiting their detectability.

In the chemical moieties useful in these methods, biological and nonbiological substances B may be incorporated into the moieties by coordination directly to Re or by attachment to a ligand of Re. Attachment may be through covalent bonding, or by electrostatic or hydrogen bonding. Many diverse means of effecting covalent bonding of substances B to ligands of Re are available. The attaching linkage may be, for example, an amide or amine bond, an ester or thioester, an ether or thioether, or any of many other linkages known to the art. The type of linkage will be determined by the substituents of the ligand and the suitable chemical groups available for bonding with the ligand on the substance that is to be labeled.

The analyte of interest and the chemical moiety may be any pair of substances which are capable of binding together in a specific manner. Such substances include, for example, whole cells, viruses, subcellular particles, nucleic acids, polysaccharides, proteins, glycoproteins, lipoproteins, lipopolysaccharides, lipids, fatty acids, peptides, cellular metabolites, hormones, pharmacological agents, tranquilizers, barbiturates, alkaloids, steroids, vitamins, amino acids, sugars, and nonbiological polymers. Of particular interest are antibody-antigen pairs. One embodiment of the invention provides the use of labeled antibodies to determine the presence of cell surface antigens, or to label particular cells for detection by cell sorting methods. Antigens immobilized by, for example, attachment to immobilized, unlabeled antibodies can be detected by labeled antibodies in a method commonly known as a "sandwich" method.

In one embodiment of the invention, B is a nucleotide or a polynucleotide. In another embodiment, B is a serum-derived antibody or a monoclonal antibody.

In competitive binding assays, B may be the same substance as the analyte of interest or an analogue of the analyte, and capable of participating in the formation of a specific complex with a complementary material. Such analytes and complementary materials include whole cells, viruses, subcellular particles, nucleic acids, polysaccharides, proteins, glycoproteins, lipoproteins, lipopolysaccharides, lipids, fatty acids, peptides, cellular metabolites, hormones, pharmacological agents, tranquilizers, barbiturates, alkaloids, steroids, vitamins, amino acids, sugars, and nonbiological polymers. Examples of such analytes and complementary materials include insulin, digoxin, dieitoxin, T4 thyroid hormone, a fungus or nematode, a serum-derived antibody or a monoclonal antibody, a DNA fragment or an RNA fragment. Of particular interest are antibody-antigen based methods. These methods are analogous to the well known radio immunoassay known to the art can, in principle, be used to advantage by employing moieties labeled according to the present invention in place of radioactively labeled compounds.

The invention further is in heterogeneous and homogeneous binding methods which utilize the chemical moieties provided herein. In heterogeneous binding methods, the bound labeled substance must be physically separated from the unbound labeled substance before measurement of the presence of label.. This is frequently accomplished in antibody-antigen systems by immobilizing one component, the antibody for example, by attachment to an insoluble matrix such as a filter or to the surface of beads or reaction vessels such as test tubes. The antigen-containing solution is poured through the filter or into the reaction vessel, and then washed away from the filter or sides of the reaction vessel. Only antigen specifically bound to antibody will remain to be determined.

In homogeneous methods, by contrast, the bound and unbound labeled material are present in the same reaction mixture when the presence of label is measured. This is possible when binding modifies the properties of the signal detectable from the label. There are many ways that luminescent labels can be used in homogeneous systems. For example, binding of the analyte to the chemical moiety can directly influence the signal detectable from the label.

Additionally, a luminescence quencher may be positioned on an antibody so that binding of a labeled antigen to the antibody could result in suppression of the luminescence of the label by the luminescence quencher on the antibody. Many homogeneous methods for luminescent labels are known to the art, and some of the are reviewed in Boguslaski and Li, "Homogeneous Immunoassays," *Applied Biochemistry and Biotechnology*, 7: 401–414 (1982).

In one embodiment of the invention, the analyte is fixed to an insoluble matrix. Such a method may be performed as a sandwich assay, i.e., the chemical moiety becomes bound to the immobilized analyte and unbound moiety is washed away from the matrix. In another embodiment a chemical agent to which the moiety is capable of binding is fixed to an insoluble matrix and the chemical moiety being a component of a biological fluid or reaction mixture. The complementary material may also be fixed to an insoluble matrix. In both the heterogeneous and homogeneous competitive methods of the invention the complementary material may be a monoclonal antibody and the insoluble matrix may the surface of an assay vessel.

The methods of the invention may be performed by exposing the reagent mixture to chemical, electrochemical, or electromagnetic energy, or the reagent mixture may be exposed to a combination of chemical, electrochemical, or electromagnetic energy.

The chemical moiety may be oxidized by exposure to an energy source. One such source is a chemical oxidizing agent. Examples of such oxidizing agents include Ce(IV) salts or $PbO_2$. The chemical moiety may be reduced by exposure to an energy source. One such energy source may be a chemical reducing agent. An example of a suitable reducing agent is magnesium. The methods of the invention include inducing the chemical moieties to emit electromagnetic radiation more than once.

The reagent mixture may comprise oxalate, pyruvate, lactate, malonate, citrate, tartrate, peroxydisulfate. Furthermore, the chemical moiety may be reduced by exposure to an energy source and the reagent mixture may comprise peroxydisulfate. Moreover, the chemical moiety may be oxidized by exposure to an energy source and the reagent mixture may comprise oxalate, pyruvate, lactate, malonate, citrate, or tartrate.

Methods of detecting the chemical moiety are provided wherein the reagent mixture is continuously exposed to an electrode whose potential oscillates between a potential sufficient to effect the reduction of said chemical moiety and a potential sufficient to effect the oxidation of the chemical moiety.

The chemical moiety may be oxidized by exposure to an electrode whose potential oscillates above and below a potential sufficient to oxidize the chemical moiety, the reagent mixture comprising oxalate, pyruvate, lactate, malonate, citrate, tartrate, peroxydisulfate. Moreover, the chemical moiety may be oxidized by exposure to an energy source and the reagent mixture may comprise oxalate, pyruvate, lactate, malonate, citrate, or tartrate.

The chemical moiety may also be reduced by exposure to an electrode whose potential oscillates above and below a potential sufficient to reduce it, the reagent mixture comprising peroxydisulfate. Such reagent mixture may additionally comprise acetonitrile. Furthermore, the chemical moiety may be reduced by exposure to an electrode whose potential is constant and sufficient to reduce it, the reagent mixture comprising peroxydisulfate. Such reagent mixture may also comprise acetonitrile.

When the chemical moiety is exposed to electrochemical or chemical energy, the emitted electromagnetic radiation may be continuously detected. Such electromagnetic radiation may be detected visually or with a photodiode. Furthermore, when the chemical moiety is exposed to electrochemical or chemical energy, the emitted radiation may be detected cumulatively, e.g., with a photographic film.

The invention includes systems for detecting or the presence or measuring the quantity of a rhenium-containing chemical moiety having formula I. The system comprises: (a) a reagent mixture comprising the rhenium-containing chemical moiety; (b) means for inducing the chemical moiety to emit electromagnetic radiation; and (c) means for detecting the emitted electromagnetic radiation.

The invention also includes systems for detecting the presence of or measuring the quantity of an analyte of interest which binds to a chemical moiety of formula I. The system comprises: (a) the rhenium-containing chemical moiety; (b) a means for contacting the chemical moiety with the analyte of interest to form a reagent mixture; (c) a means for inducing the chemical moiety to emit electromagnetic radiation; and (d) a means for detecting the emitted electromagnetic radiation.

A particularly unique and useful class of homogeneous binding assays is provided by the present invention. As described hereinbefore, these labels can be measured electrochemically by means of exposing a solution of the labeled substance of interest to an electrode. Any labeled substance which is present in the solution but which cannot gain access to the surface of the electrode will not be detected. This can occur, for example, if the labeled substance is bound directly or indirectly to the surface of the reaction vessel into which the electrode is placed, or if the label is embedded deep into the interior of the specific complex, such as within an antigen-antibody complex, or if the electrode itself were coated with a layer through which labeled material could pass but complexed labeled material could not pass. In addition, it should be possible to coat the surface of an electrode with antibodies, so that only labeled antigen bound to the immobilized antibodies can obtain access to the electrode and thereby be determined. This particular homogeneous method may be most effective if the required electrode potential is applied in short pulses.

It is within the scope of the present invention to use a combination of means for determining the presence of labeled compounds. For example, it may be desirable to measure the total amount of labeled substance by a means which does not distinguish between bound and unbound labeled substance such as photoluminescence or chemiluminescence, and to determine the amount of bound labeled substance by a means which does distinguish between bound and unbound labeled substance, such as electrochemiluminescence, for example. Such a combination of methods could be performed on the same sample, and thus provide a richer source of information about the sample than could any method when used individually. It is also within the scope of this invention to determine the presence of two or more differently labeled compounds within the same reaction mixture. This is possible either if the labels emit electromagnetic radiation of differing wavelengths or if the labels can be induced to emit electromagnetic radiation by exposure to energy of different values or source.

Assay Methods

The invention also is in improved methods of detecting in a predetermined volume of a multicomponent, liquid sample an analyte of interest present in the sample at a concentration below about $10^{-3}$ molar which comprises: (a) contacting a sample with a reagent comprising an electrochemiluminescent chemical moiety containing a rhenium-containing organic compound wherein said reagent is (i) capable of being induced to repeatedly emit electromagnetic radiation upon exposure to an amount of chemical, electrochemical, or electromagnetic energy from a suitable source effective to induce the reagent to repeatedly emit radiation and (ii) capable of combining with the analyte of interest, the contact being effected under appropriate conditions such that the analyte and the reagent combine; (b) exposing the resulting sample to an amount of chemical, electrochemical, or electromagnetic energy from a suitable source effective to induce the reagent to repeatedly emit radiation, the exposure being effected under suitable conditions so as to induce the reagent to repeatedly emit electromagnetic radiation; and (c) detecting electromagnetic radiation so emitted and thereby detecting the presence of the analyte of interest in the sample.

The term "molar" means the concentration of an analyte in solution in moles per liter or the amount of particulate matter present in a liquid sample in particles or units per liter. For example, $1 \times 10^{23}$ particles per liter may be expressed as 1 molar.

The methods may be performed as heterogeneous assays, i.e., assays in which unbound labeled reagent is separated from bound labeled reagent prior to exposure of the bound labeled reagent to electrochemical energy, and homogeneous assays, i.e., assays in which unbound labeled reagent and bound labeled reagent are exposed to electrochemical energy together. In the homogeneous assays of the present invention the electromagnetic radiation emitted by the bound labeled reagent is distinguishable from the electromagnetic radiation emitted by the unbound labeled reagent, either as an increase or as a decrease in the amount of electromagnetic radiation emitted by the bound labeled reagent in comparison to the unbound labeled reagent, or as electromagnetic radiation of a different wavelength.

Accordingly, in one embodiment of the invention any reagent which is not combined with the analyte of interest is separated from the sample, which had been contacted with the reagent, prior to exposure of the sample to electrochemical energy. In another embodiment of the invention, prior to contacting the sample with the reagent, the sample is treated so as to immobilize the analyte of interest.

Means for immobilizing analytes of interest are well known within the art and include contacting the sample with a polystyrene, nitrocellulose or nylon surface, or a surface coated with whole cells, subcellular particles, viruses, prions, viroids, lipids, fatty acids, nucleic acids, polysaccharides, proteins, lipoproteins, lipopolysaccharides, glycoproteins, peptides, cellular metabolites, hormones, pharmacological agents, tranquilizers, barbiturates, alkaloids, steroids, vitamins, amino acids, sugars, nonbiological polymers, synthetic organic molecules, organometallic molecules or inorganic molecules. The analyte of interest may be any of these substances, or the analyte of interest may be a whole cell, subcellular particle, virus, prion, viroid, nucleic acid, protein, lipoprotein, lipopolysaccharide, glycoprotein, peptide, hormone, pharmacological agent, nonbiological polymer, synthetic organic molecule, organometallic molecule or an inorganic molecule present in the sample at the concentration below about $10^{-12}$ molar. The analyte of interest may be a whole cell, subcellular particle, virus, prion, viroid or nucleic acid present in the sample at a concentration below about $10^{-15}$ molar.

The reagent which is contacted with the sample is a Re-containing electrochemiluminescent chemical moiety conjugated to a whole cell, subcellular particle, virus, prion, viroid, lipid, fatty acid, nucleic acid, polysaccharide, protein, lipoprotein, lipopolysaccharide, glycoprotein, peptide, cellular metabolite, hormone, pharmacological agent, tranquilizer, barbiturate, alkaloid, steroid, vitamin, amino acid, sugar, nonbiological polymer, synthetic organic molecule, organometallic molecule, inorganic molecule, biotin, avidin or streptavidin. In one embodiment of the invention the agent is an electrochemiluminescent moiety conjugated to an antibody, antigen, nucleic acid, hapten, ligand or enzyme, or biotin avidin or streptavidin.

The sample may be derived from a solid, emulsion, suspension, liquid or gas. Furthermore, the sample may be derived from water, food, blood, serum, urine, feces, tissue, saliva, oils, organic solvents or air. Moreover, the sample may comprise acetonitrile, dimethylsulfoxide, dimethylformamide, n-methylpyrrolidone or tert-butyl alcohol. The sample may comprise a reducing agent or an oxidizing agent.

The invention is also in improved competitive methods for detecting in a predetermined volume of a multicomponent, liquid sample an analyte of interest present in the sample at a concentration below about $10^{-3}$ molar which comprises: (a) contacting a sample with a reagent comprising an electrochemiluminescent chemical moiety containing a rhenium-containing organic compound wherein said reagent is (i) capable of being induced to repeatedly emit electromagnetic radiation upon exposure to an amount of chemical, electrochemical, or electromagnetic energy from a suitable source effective to induce the reagent to repeatedly emit radiation and (ii) capable of competing with the analyte of interest for binding sites on a complementary material not normally present in the sample, and with the complementary material, the contact being effected under appropriate conditions such that the analyte of interest and the reagent competitively bind to the complementary material; (b) exposing the resulting sample to an amount of chemical, electrochemical, or electromagnetic energy from a suitable source effected to induce the reagent to repeatedly emit radiation, the exposure being effected under suitable conditions so as to induce the reagent to repeatedly emit electromagnetic radiation; and (c) detecting electromagnetic radiation so emitted and thereby detecting the presence of the analyte of interest in the sample.

The reagent may be the analyte of interest conjugated to an electrochemiluminescent chemical moiety or an analogue of the analyte of interest conjugated to an electrochemiluminescent moiety.

The complementary material may be a whole cell, subcellular particle, virus, prion, viroid, lipid, fatty acid, nucleic acid, polysaccharide, protein, lipoprotein, lipopolysaccharide, glycoprotein, peptide, cellular metabolite, hormone, pharmacological agent, tranquilizer, barbiturate, steroid, vitamin, amino acid, sugar, nonbiological polymer, synthetic organic molecule, organometallic molecule or inorganic molecule.

The methods provided herein may be performed so as to determine the quantity of an analyte of interest in a predetermined volume of a multicomponent, liquid sample. The method comprises: (a) contacting the sample with a known amount of a reagent comprising an electrochemiluminiscent chemical moiety containing a rhenium-containing organic compound wherein said reagent is (i) capable of being induced to repeatedly emit electromagnetic energy from a suitable source effective to induce the reagent to repeatedly emit radiation and (ii) capable of combining with the analyte of interest, the contact being effected under appropriate conditions such that the analyte and reagent combine; (b) exposing the resulting sample to an amount of chemical, electrochemical, or electromagnetic energy from a suitable source effective to induce the reagent to repeatedly emit electromagnetic radiation; and (c) quantitatively determining the amount of radiation so emitted and thereby quantitatively determining the amount of the analyte of interest present in the sample.

This method may be performed as a heterogeneous assay or as a homogeneous assay. In one embodiment of the invention any reagent which is not combined with the analyte of interest is separated from the sample, which had been contacted with a known amount of the reagent, prior to the exposure of the sample to an amount of electrochemical energy from a suitable source effective to induce the reagent to repeatedly emit radiation. In yet another embodiment of the invention, prior to contacting the sample with the reagent, the sample is treated so as to immobilize the analyte of interest.

The analyte of interest may be a whole cell, subcellular particle, virus, prion, viroid, lipid, fatty acid, nucleic acid, polysaccharide, protein, lipoprotein, lipopolysaccharide, glycoprotein, peptide, cellular metabolite, hormone, pharmacological agent, tranquilizer, barbiturate, steroid, vitamin, amino acid, sugar, nonbiological polymer, synthetic organic molecule, organometallic molecule or inorganic molecule.

The reagent with which the sample is contacted may be an electrochemiluminescent chemical moiety conjugated to a whole cell, subcellular particle, virus, prion, viroid, lipid, fatty acid, nucleic acid, polysaccharide, protein, lipoprotein, lipopolysaccharide, glycoprotein, peptide, cellular metabolite, hormone, pharmacological agent, tranquilizer, barbiturate, steroid, vitamin, amino acid, sugar, nonbiological polymer, synthetic organic molecule, organometallic molecule or inorganic molecule.

In one embodiment of the invention the reagent is a Re-containing electrochemiluminescent chemical moiety conjugated to an antibody, antigen, nucleic acid, hapten, ligand or enzyme, or biotin, avidin, or streptavidin.

The sample may be derived from a solid, emulsion, suspension, liquid or gas. Samples which comprise the analyte of interest may be derived from water, food, blood, serum, urine, feces, tissue, saliva, oils, organic solvents or air. Additionally, samples may comprise acetonitrile, dimethylsulfoxide, dimethyulformamide, n-methylpyrrolidinone or tert-butyl alcohol. Furthermore, the sample may comprise a reducing agent or an oxidizing agent.

The invention is also in a competitive method for quantitatively determining in a predetermined volume of a multicomponent, liquid sample the amount of an analyte of interest present in the sample. This method comprises: (a) contacting the sample with a known amount of a reagent comprising an electrochemiluminescent chemical moiety containing a rhenium-containing organic compound wherein said reagent is (i) capable of being induced to repeatedly emit electromagnetic radiation upon exposure to an amount of chemical, electrochemical, or electromagnetic energy from a suitable source effective to induce the reagent to repeatedly emit radiation and (ii) capable of competing with the analyte of interest for binding sites on a complementary material not normally present in the sample, and with a known amount of the complementary material, the contact being effected under appropriate conditions such that the analyte of interest and the reagent competitively bind to the complementary material; (b) exposing the resulting sample to an amount of electrochemical energy from a suitable source effective to induce the reagent to repeatedly emit radiation, the exposure being effected under suitable conditions so as to induce the reagent to repeatedly emit electromagnetic radiation; and (c) quantitatively determining the amount of radiation so emitted and thereby quantitatively determining the amount of the analyte of interest present in the sample.

In one embodiment of the invention, the reagent is the analyte of interest conjugated to an electrochemiluminescent chemical moiety or an analogue of the analyte of interest conjugated to an electrochemiluminescent chemical moiety.

The complementary material may be a whole cell, subcellular particle, virus, prion, viroid, lipid, fatty acid, nucleic acid, polysaccharide, protein, lipoprotein, lipopolysaccharide, glycoprotein, peptide, cellular metabolite, hormone, pharmacological agent, tranquilizer, barbiturate, steroid, vitamin, amino acid, sugar, nonbiological polymer, synthetic organic molecule, organometallic molecule or inorganic molecule.

The invention is also in methods for detecting and identifying the presence of a multiplicity of analytes of interest in a liquid food or food homogenate. These methods comprise: (a) immersing into the liquid food or food homogenate a portion of a diagnostic reagent holder suitable for immersing into a liquid or solid suspension and having immobilized it to a multiplicity of reagents, each reagent being immobilized to the diagnostic reagent holder in distinct, identifiable regions and capable of forming a complex with a single analyte of interest so as to allow the formation of immobilized reagent-analyte of interest complexes; (b) removing the diagnostic reagent holder from the liquid food or food homogenate; (c) rinsing the diagnostic reagent holder with a suitable rinsing solution; (d) immersing the portion of the diagnostic reagent holder which contains the immobilized reagent-analyte of interest complexes into a detection reagent capable of forming complexes with the immobilized reagent-analyte of interest complexes so as to allow the formation of immobilized reagent-analyte of interest-detection reagent complexes; and (e) detecting the presence on the identifiable regions of the diagnostic reagent holder to which reagents are immobilized of immobilized reagent-analyte of interest-detection reagent complexes, thereby detecting and identifying the presence of a multiplicity of analytes of interest in the liquid food or food homogenate.

The analytes of interest may be microorganisms. The microorganisms may be viable or nonviable or may be bacteria. Examples of bacteria which may be detected by this method include, but are not limited to, Salmonella, Campylobacter, Escherichia, Yersinia, Bacillus, Vibrio, Legionella, Clostridium, Streptococcus or Staphylococcus.

The analytes of interest may be antigens. Such antigens include, but are not limited to, enterotoxins and aflatoxins.

The immobilized reagents and the detection reagents may be polyclonal antibodies, monoclonal antibodies, mixtures of monoclonal antibodies, or mixtures of polyclonal and monoclonal antibodies.

The detection reagents are labeled with a detectable marker comprising an electrochemiluminescent chemical moiety containing a rhenium-containing organic compound capable of being induced to repeatedly emit electromagnetic radiation upon exposure to an amount of chemical, electrochemical, or electromagnetic energy from a suitable source effective to induce the moiety to emit radiation.

The invention includes methods for detecting and identifying the presence of a multiplicity of Staphylococcal enterotoxins in a liquid or solid suspension. These methods comprise: (a) immersing a diagnostic reagent holder provided with a multiplicity of monoclonal antibodies specific for Strephylococcal enterotoxins and which are separately and distinctly immobilized to it into the liquid or solid suspension for a suitable length of time so as to allow the formation of immobilized monoclonal antibody-Staphylococcal enterotoxin complexes; (b) removing the diagnostic reagent holder from the sample; (c) immersing the diagnostic holder into a buffered aqueous solution which comprises a surfactant; (d) removing the diagnostic reagent holder from the buffered aqueous solution which contains a surfactant; (e) immersing the diagnostic reagent holder into a detection solution which comprises a monoclonal antibody-alkaline phosphatase conjugate for a suitable length of time as to allow the formation of immobilized monoclonal antibody-Staphylococcal enterotoxin-monoclonal antibody-alkaline phosphatase complexes; (f) removing the diagnostic reagent holder from the detection solution; (g) immersing the diagnostic reagent holder into a buffered aqueous solution; (h) removing the diagnostic reagent holder from the buffered aqueous solution; (i) immersing the diagnostic reagent holder into a solution which comprises 5-bromo, 4-chloro indolyl phosphate and nitroblue tetrazolium; (j) visibly detecting the identifiable regions of the nitrocellulose membrane onto which a blue precipitate accumulates; (k) correlating the identifiable regions of the nitrocellulose membrane onto which a blue precipitate accumulates with the Staphylococcal enterotoxin for which the monoclonal antibody immobilized to the region is specific, thereby indicating the presence and the identity of a multiplicity of the Staphylococcal enterotoxins in the sample.

The reagent capable of forming a complex with the immobilized bacterial components may be a polyclonal antibody, a monoclonal antibody, a mixture of monoclonal antibodies or a mixture of polyclonal and monoclonal antibodies. The reagent is labeled with a detectable marker comprising an electrochemiluminiscent moiety containing a Re-containing organic compound capable of being induced to repeatedly emit electromagnetic radiation upon exposure to an amount of chemical, electrochemical, or electromagnetic energy.

In yet another embodiment of the invention, the immobilized bacterial component-reagent complexes may be detected with a detectably marked second reagent capable of forming a complex with the immobilized bacterial component-reagent complexes. In still another embodiment of the invention the reagent may be a polyclonal antibody, a monoclonal antibody, a mixture of monoclonal antibodies or a mixture of polyclonal and monoclonal antibodies and the second reagent may be a detectably marked antiantibody directed to the reagent.

Samples in which bacteria may be detected include water and food.

EXAMPLES

Introduction

Materials and Methods

Ligands 2,2'-bipyridine (BPY) (Aldrich) was used without further purification. 4,4'-dimethyl-2,2'-bipyridine (Me$_2$bpy) (Reilly Tar Chemicals) was sublimed (90°–100° C., 10$^{-3}$ torr) prior to use. 4,4'-diphenyl-2,2'-bipyridine (Ph$_2$bpy) (Aldrich) was recrystallized once from benzene/petroleum ether prior to use. 4-ethyl pyridine (Etpy) (Aldrich) was used without further purification. Other pyridyl and bipyridyl ligands used included:

4,4'-bis(N,N-diethylamino)-2,2'-bipyridine [(NEt$_2$)$_2$bpy] (Maeker, G., and Case, F. H., *J. Amer. Chem. Soc.* 80:2745 (1958));

4,4'-(dimethoxy)-2,2'-bipyridine [(CH$_3$—O)$_2$bpy] (Wenkert, D., Woodward, R. B., *J. Org. Chem.* 48:283 (1983));

4,4',5,5'-tetramethyl-2,2'-bipyridine (Me$_4$bpy) (Elliot, M. C., Freitag, R. A., Blaney, D. D., *J. Amer. Chem. Soc.* 107:4647 (1985);

4,4'-dichloro-2,2'-bipyridine (Cl$_2$bpy) (Wenkert, D., Woodward, R. B. (1983), supra);

4,4'-bis (carbomethoxy)-2,2'-bipyridine ((CO$_2$CH$_3$)$_2$bpy) (Maeker, G., and Case, F. H. (1958), supra);

4,4'-dinitro-2,2'-bipyridine ((NO$_2$)-$_2$bpy) (Maeker, G., and Case, F. H. (1958), supra);

Solvents

Methylene chloride (CH$_2$Cl$_2$), petroleum ether, diethyl ether (anhydrous), and methanol were all Chempure grade from Curtin Matheson Scientific (Florence, N.Y.) and were used as received. Acetone (A. C. S. Reagent Grade) and acetonitrile (Omni-Solv) from EM Scientific (Cherry Hill, N.J.) were used without further purification. Benzene was A. C. S. Reagent Grade from Fisher Scientific (Springfield, N.J.) and was used as received. Toluene (Baker Analyzed Reagent, HPLC grade) from J. T. Baker Chemicals (Phillipsburg, N.J.) was used without further purification. Tetrahydrofuran from J. T. Baker Chemicals was dried by distillation from sodium/benzophenone under argon atmosphere immediately prior to use. Anhydrous ethanol (200 proof) was obtained from the Warner-Graham Co. (Cockeyesville, Md.). 2-methoxyethanol (Aldrich HPLC grade) was used as received. Pyridine (Aldrich Gold Label) was obtained in the anhydrous form and stored in Sure-Seal® (Aldrich) bottles until used. Dimethylformamide (DMF) was A. C. S. Reagent Grade (DMF) and was used as received. Water was deionized using the Millipore-Milli-Q system.

Chromatography

Neutral absorption alumina (Fisher) was used as received. Ottawa sand and glass wool for chromatography were obtained from Aldrich. Sephadex LH-20 was purchased from Pharmacia and was activated for use by suspending in stirred methanol for 12 hours immediately prior to use. SP-Sephadex C-25 (Sigma, St. Louis, Mo.) was activated by stirring in boiling water for 2 hrs. immediately prior to use.

Other Reagents

Sodium metal, benzophenone (Gold Label), trifluoromethane sulfonic acid (HO$_3$SCF$_3$, i.e., triflic acid), and silver trifluoromethane sulfonate (AgCF$_3$SO$_3$, i.e., silver triflate) were all used as received from Aldrich. Trifluoromethane sulfonic anhydride ((CF$_3$SO$_2$)$_2$O) (Alfa-Ventron, Danvers, Mass.) was used as obtained. Ammonium hexafluorophosphate (NH$_4$PF$_6$) (Aldrich) was used without further purification. NaCl and NaClO$_4$ were both A. C. S. reagent grade from Fisher Scientific and were used as received. Pentacarbonyl rhenium (I) chloride, (CO)$_5$ReCl, was purchased from Pressure Chemical Co. (Pittsburgh, Pa.). Anhydrous sodium sulfate and indicating Drierite® (CaSO$_4$, anhydrous) were obtained from Aldrich. Argon gas from Robert's Oxygen Co. (Rockville, Md.) was dried by passage through a column (3 inch i.d.×12 inch height) of indicating Drierite® prior to use.

1,3-dimethyl-4,5-diaminouracil (DADMU) from Aldrich was recrystallized from methanol/petroleum ether under argon prior to use. Anhydrous LiClO$_4$ and isonicotinoyl chloride hydrochloride were used as received from Aldrich. A. C. S. Reagent grade NaOH from Fisher was used without further purification. Isopropanol (Chempure brand) from Curtin Matheson Scientific was used as received.

Synthesis of Model Re(I) Complexes

The general synthetis scheme for luminescent Re(I) complexes is illustrated in FIG. 1. The starting material for the preparation of the luminescent Re(I) complexes was Re(CO)$_5$Cl. The synthesis of the dried Re(I) species involved two steps. In the first step, substitution of CO by chelating 2,2'-bipyridine ligand produces the facial isomer, fac-(L)Re(CO)$_3$Cl. L is a chelating 2,2'-bipyridine ligand, e.g., bpy, Cl$_2$bpy, (CO$_2$CH$_3$)$_2$bpy, (NO$_2$)$_2$bpy, Me$_2$bpy, Ph$_2$bpy, (CH$_3$O)$_2$bpy, Me$_4$bpy, or (NEt$_2$)$_2$bpy. The general synthesis procedure is described below.

To a 250 ml flask equipped with reflux condenser and stir bar were added 361.7 mg (1 mmol) of (CO)$_5$ReCl, 1.02 mmol of the desired bipyridyl ligand, e.g., 187 mg Me$_2$bpy, and 80–100 ml toluene. The solution was argon bubble degassed for 15 min. and refluxed under an argon atmosphere for 90 min. with stirring. During this time, the product usually precipitates from solution. After the flask was cooled to room temperature the precipitated product was collected by suction filtration, washed twice with 15 ml portions of cold toluene followed by three 15 ml portions of diethyl ether, and air suction dried for 30 min. Drying was completed in a vacuum desiccator over CaSO$_4$ overnight. If precipitation of the product did not occur on cooling, dropwise addition of diethyl ether to the stirred toluene solution induced precipitation. The product obtained from this reaction was analytically pure. The yield of product fac-(1)Re(CO)$_3$Cl was greater than 90% based on initial (CO)$_5$ReCl.

The conversion of fac-(L)Re(CO)$_3$ to the corresponding fac-(L)Re(CO)$_3$(Etpy) (R) (where R is CF$_3$CO$_3$$^-$, PF$_6$$^-$, ClO$_4$$^-$) was accomplished by either of the following two methods.

Method I—Acid Method

This method is useful for bipyridyl ligands that are insensitive, i.e., stable, to strongly acidic media. It involves the production and isolation of the intermediate Re(I) triflate species followed by conversion to the 4-pyridyl ethane derivative. The following example illustrates the procedure:

Preparation of fac-[(NEt$_2$)$_2$bpy]Re(CO$_3$SCF$_3$)

To a 250 ml round bottom flask equipped with stir bar were added 456 mg (0.75 mmol) of fac-[(NEt$_2$)$_2$bpy]Re(CO)$_3$Cl and 30 ml of methylene chloride. To the stirred suspension were added 1.34 ml (20 times amount required) of trifluoromethane sulfonic acid HO$_3$SCF$_3$, and 3–5 drops of trifluoromethane sulfonic anhydride, (CF$_3$SO$_2$)$_2$O. The solid immediately dissolved to give a dark yellow solution. The flask was stoppered and the solution stirred at a room temperature for 3 hrs., after which time the product was isolated by adding 200 ml of anhydrous diethyl ether dropwise to the stirred solution. The yellow product, fac-[(NEt$_2$)$_2$bpy]Re(CO)$_3$(O$_3$SCF$_3$), was isolated via suction filtration. The precipitated product was washed with six 30 ml portions of anhydrous diethyl ether to remove traces of trifluoromethane sulfonic acid and air suction dried for 30 min. Drying was completed in the vacuum desiccator over CaSO$_4$ overnight. The yield was 500 mg of [(NEt$_2$)$_2$bpy]Re(CO)$_3$(O$_3$SCF$_3$) (93% based on [(NEt$_2$)$_2$bpy]Re(CO)$_3$Cl. The product was sufficiently pure for use in subsequent reactions. The Re(I)-triflate species just described may be converted to the corresponding Etpy complex as shown in FIG. 3. The following illustrates the procedure.

Preparation of fac-[(NEt$_2$)$_2$bpy]Re(CO)$_3$(Etpy)(CF$_3$SO$_3$)

Into a 250 ml round bottom flask equipped with stir bar and reflux condenser were added 150 mg. (0.2 mmol) of fac-[(NEt$_2$)$_2$bpy]Re(CO)$_3$(O$_3$SCF$_3$) and 50 ml ethanol. To this mixture were added 0.24 ml (10 times the amount required) of 4-pyridyl ethane. The solution was argon bubble degassed for 15 min. and refluxed under an argon atmosphere with stirring for 2 hours. After the solution cooled to room temperature, the ethanol was removed by evaporation using a rotary evaporator (Buchi Model RE-121). The remaining sample consisted of the crude product fac-[(NEt$_2$)$_2$bpy]Re(CO)$_3$(Etpy)(CF$_3$SO$_3$), dissolved in the excess 4-pyridyl ethane. The sample was dissolved in a minimum volume (5–15 ml) of 1:2 (v/v) CH$_3$CN/toluene and chromatographed on neutral alumina (adsorption alumina, Fisher Scientific) using a 30 cm×3 cm i.d. column. Elution with 1:2 (v/v) CH$_3$CN/toluene removed excess 4-pyridyl ethane ligand. The yellow product band, fac-[(NEt$_2$)$_2$bpy]Re(CO)$_3$(Etpy)(CF$_3$SO$_3$), was eluted with 1:1 (v/v) CH$_3$CN/toluene. Although some tailing was observed, complete separation from a small amount of an unidentified purple species was achieved. The solvent fraction containing the product was evaporated to dryness on the rotary evaporator. The residue was dissolved in 5 ml methylene chloride and the solvent evaporated again using the rotary evaporator. Pale yellow flakes of fac-[(NEt$_2$)$_2$bpy]Re(CO)$_3$(Etpy)(CF$_3$SO$_3$) were obtained in 50% yield (based on starting [(NEt$_2$)$_2$bpy]Re(CO)$_3$(O$_3$SCF$_3$)]. The product is analytically pure.

| | C$_{30}$G$_{36}$N$_4$O$_6$SF$_3$Re | | | |
|---|---|---|---|---|
| | C | H | N | O |
| Theory | 42.24 | 4.24 | 8.50 | 11.64 |
| Found | 42.90 | 4.51 | 8.24 | 11.99 |

Method II—Silver Method

The silver method is used for complexes containing bipyridyl ligands susceptible to decomposition in highly acidic environments, e.g., L=(CH$_3$O)$_2$bpy or (COOCH$_3$)$_2$bpy. In this method a soluble silver trifluoromethane sulfonate salt was reacted with the fac-(L)Re(CO)$_3$Cl species to form the fac-(L)Re(CO)$_3$(O$_3$SCF$_3$) moiety and insoluble AgCl. After removal of the AgCl precipitate by filtration, the solution was reacted in situ with 4-pyridyl ethane to produce the desired product. No attempts were made to isolate the intermediate fac-(L)Re(CO)$_3$(O$_3$SCF$_3$) salts in this procedure. The following illustrates the method:

Preparation of fac-[Cl$_2$bpy]Re(CO)$_3$(Etpy)(CF$_3$SO$_3$)

Because silver trifluoromethane sulfonate, AgCF$_3$SO$_3$, is light sensitive, all operations were performed in a darkened area under red safelight.

Tetrahydrofuran (THF) was dried by reflux under an argon atmosphere over Na/benzophenone for 90 min. The solvent was collected by distillation immediately prior to use.

Into a dry 250 ml round bottom flask equipped with stirbar and reflux condenser were added 500 mg (0.94 mmol) fac-(Cl$_2$bpy)Re(CO)$_3$Cl, 242 mg. (0.94 mmol) AgCF$_3$SO$_3$ and 100 ml of dry THF. The contents of the flask were argon bubble degassed for 15 min. and refluxed under argon atmosphere with stirring for 3 hrs., at which time the contents of the flask were suction filtered using a glass fritted funnel (fine porosity) to remove the AgCl precipitate. The AgCl precipitate was washed three times with 15 ml portions of methanol. The CH$_3$OH washings were combined with the filtrate and added to a clean 250 ml round bottom flask equipped with stirbar. 0.75 g (6.59 mmol) of 4-pyridyl ethane were added, the solution was argon bubble degassed for 15 min. and refluxed under argon atmosphere for 2 hrs.

After the orange-brown solution cooled to room temperature the methanol and THF were removed using the rotary evaporator. The product slurry that remained was purified by either of the following two methods:

Procedure 1

An alumina column (15 inch height×2 inch i.d.) with 1:2 (v/v) CH$_3$CN/toluene was prepared as described in Method I for the purification of fac-[(NEt$_2$)$_2$bpy]Re(CO)$_3$ (Etpy)(CF$_3$SO$_3$). The sample was dissolved in 10–15 ml of 1:2 (v/v) CH$_3$CN/toluene and loaded into the column. Elution with 1:2 (v/v) CH$_3$CN/toluene removed a small yellow band identified as (Cl$_2$bpy) Re(CO)$_3$Cl. Elution with 1:1 (v/v) CH$_3$CN/toluene removed a compact orange-brown band. This overlap limits the yield of the reaction to 17% based on fac-(CL$_2$bpy)Re(CO)$_3$Cl. Although the yellow product band tailed, it separated cleanly from a number of trailing yellow, purple, and brown bands on the column. No attempt was made to isolate or identify these side products. Isolation of the fac-(Cl$_2$bpy)Re(CO)$_3$(Etpy)(CF$_3$SO$_3$) product was identical to that described for fac-[(NEt$_2$)$_2$bpy]Re(CO)$_3$(Etpy) (CF$_3$SO$_3$) in Method I.

Procedure 2

An improved yield of complex was obtained through the use of ion exchange chromatography as a purification procedure. A column (2 cm i.d.×30 cm length) of SP-Sephadex C-25 ion exchange resin was prepared in water. The slurry obtained from the product workup was mixed with approximately 10 ml H$_2$O and acetone was added dropwise until a homogeneous solution was observed. SP-Sephadex C-25 resin was added to the crude product slurry solution until the product was absorbed onto the resin. The acetone was removed by evaporation using the rotary evaporator. The resin containing the absorbed reaction products was loaded onto the column. Elution with H$_2$O removed 4-pyridyl ethane and uncharged fac-(Cl$_2$bpy)Re(CO)$_3$(Etpy)$^+$ cation was eluted as the Cl$^-$ salt using aqueous 0.25M NaCl solution. The side products of the reaction remained on the column. The product was isolated as the PF$_6^-$ salt by addition of saturated aqueous NH$_4$PF$_6$ solution dropwise to the 0.25M NaCl solution containing the product. The fac-(Cl$_2$bpy)Re(CO)$_3$(Etpy)(PF$_6$) precipitate was collected by suction filtration on a glass fritted filter (medium porosity). The product was suspended in 10 ml H$_2$O containing 1 drop saturated NH$_4$PF$_6$ solution. Acetone was added until the solid completely dissolved. The complex was precipitated in pure form by slow evaporation of the acetone at room temperature on the rotary evaporator. The complex was collected by suction filtration on the glass fritted filter (medium porosity) and washed with 10 ml ice cold H$_2$). The complex was then washed with two 15 ml portions of diethyl ether and air suction dried for 30 min. Drying was completed over CaSO$_4$ in the vacuum desiccator overnight. A yield of 24% based on (Cl$_2$bpy)Re(CO)$_3$Cl was obtained. The small, bright yellow crystals of fac-(Cl$_2$bpy)Re(CO)$_3$(Etpy)(PF$_6$) were analytically pure.

| | C$_{20}$H$_{14}$N$_3$O$_3$Cl$_2$RePF$_6$ | | |
|---|---|---|---|
| | C | H | N |
| Theory | 32.14 | 2.02 | 5.62 |
| Found | 32.80 | 2.12 | 5.49 |

In general, complexes containing electron-releasing substituents such as NEt$_2$, CH$_3$O, CH$_3$, etc., react cleanly and are readily purified using Procedure 1. Complexes containing electron-withdrawing substituents such as Cl or NO$_2$ on the 2,2'-bipyridine ligand are best purified using Procedure 2. The electron withdrawing nature of the 2,2'-bipyridine ligand in such complexes abstracts electron density from the formal Re(I) center. The resulting increase in partial positive charge at the Re center results in a greater electrostatic attraction between the Re(I) and Cl⁻. The strengthening of the Re—Cl bond that results decreases the effectiveness of Cl⁻ as a leaving group in the presence of silver cation, Ag⁺ or HO₃SCF₃. Consequently, attack of these species at other points within the Re(I)—Cl complex to generate side products becomes competitive with simple Cl⁻ displacement. The charged products which apparently result are best separated using ion exchange resins.

A summary of the fac-(L)Re(CO)₃(Etpy)(CF₃SO₃) complexes synthesized to date, as well as yields after purification and methods of preparation (Acid—Method I; Silver—Method II), is shown in FIG. 4. Emission maxima for the complexes in CH₃CN are also listed. Emission spectra were obtained using a Perkin-Elmer Model LS-5 spectrofluorimeter.

The emission spectra were not corrected for variations in detector sensitivity with wavelength and are meant only to provide a qualitative illustration of the emission wavelength range which is accessible using these compounds.

Two luminescent Re(I)-theophylline species have also been prepared as model sensor-analyte conjugates. The preparations are described as below:

EXAMPLE I

Preparation of theophylline-8-butyric acid, 3-propylpyridylamide (T8BA3PPA): Compound I 0.163 g (1.2 mmol) of 3-(4 pyridyl)-propylamine were combined with 0.776 g (1 mmol) of dicyclohexylcarbodiimide in 10 ml of anhydrous pyridine. The resulting solution was allowed to stir overnight. Precipitated dicyclohexyl urea was filtered off and the filtrate was concentrated under vacuum. The remaining solid was dissolved by boiling in 50% aqueous isopropanol. On cooling a small amount of solid had fallen out which was filtered off. The filtrate was concentrated to yield an oil that slowly solidified on standing. The solid was dissolved in 10 ml 0.1N HCl and again filtered to remove a small amount of insoluble materials. The pH was then adjusted to 7 with aqueous sodium carbonate. The solution was cooled on ice and a crystalline white product was obtained (yield 0.149 g, 39%). The product was characterized by elemental analysis and proton NMR to reveal the following structure:

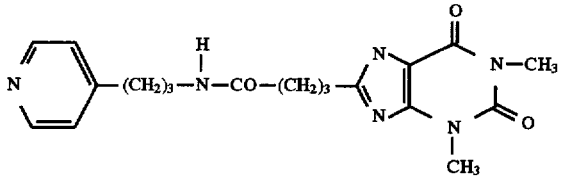

EXAMPLE II

Preparation of fac-(bpy)Re(CO)₃(T8BA3PPA)(ClO₄): Compound II

Fac-(bpy)Re(CO)₃(O₃SCF₃) was prepared as described above using the acid procedure (Method I).

Into a 100 ml round bottom flask equipped with stirbar and condenser were added 155 mg (0.27 mmol) fac-(bpy) Re(CO)₃(O₃SCF₃), 129 mg (0.37 mmol) Compound I, 20 ml H₂O and 20 ml ethanol. The solution was argon bubble degassed for 15 min. and refluxed under argon atmosphere for 3 hrs. After cooling to room temperature, the solvent was evaporated on a rotary evaporator. The dry solid was dissolved in 10–15 ml of methanol and 0.2 g anhydrous LiClO₄ were added. When the LiClO₄ was dissolved the solution was transferred to a Sephadex LH-20 column (75 cm height×2 cm i.d.) for chromatographic purification. The column was equilibrated with methanol. The sample was run at a flow rate of between 0.1–0.2 ml/min. Three bands separated. The leading band fluoresced at 567 nm in CH₃OH and was the desired product (Compound II). It separated cleanly from the remaining bands. No effort was made to identify the minor products represented by these bands. The product was isolated by evaporation of CH₃OH on the rotary evaporator. The complex was dissolved in 5 ml CH₃OH and gravity dripped into 150 ml stirring anhydrous diethyl ether. The complex was precipitated as a light yellow-green powder. It was collected by suction filtration on a glass fritted filter (medium porosity) and washed with two 15 ml portions of anhydrous diethyl ether. Air suction drying was avoided. Drying was completed in the vacuum desiccator over CaSO₄ overnight. A 48% yield of Compound II was obtained based on fac-(bpy)Re(CO)₃(O₃SCF₃). The complex was analytically pure.

| C₃₂H₃₂N₈O₁₀ClRe [910.05 gt/mmol] | | | | | |
|---|---|---|---|---|---|
| | C | H | N | O | Cl |
| Theory | 42.23 | 3.52 | 12.32 | 17.58 | 3.90 |
| Found | 41.72 | 4.00 | 12.58 | 17.98 | 3.74 |

The product had the following structure.

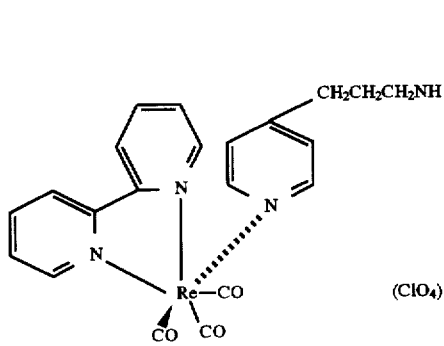 (ClO₄)

EXAMPLE III

Preparation of 1,3-dimethyl-4-amino-5-(isonicotinylamide)-uracil: Compound III

Compound III was prepared by the reaction of isonicotinyl chloride hydrochloride (INC) with 1,3-dimethyl-4,5-diamino uracil (DADMU) in dry pyridine as described below.

DADMU was purified by recrystallization from methanol under argon atmosphere and dried overnight over CaSO₄ in the vacuum desiccator. The pale yellow compound was stored under argon.

A 100 ml round bottom flask equipped with stirbar was deaerated with argon gas and cooled in an ice bath. Using a syringe, 35 ml dry pyridine were added and the system deaerated with argon. After 15 min. 1.04 g (5.84 mmol) of isonicotinoyl chloride hydrochloride were added in three portions over a 15 min. interval. Dissolution to a brown solution occurred. To this solution were added 0.98 g (5.76 mmol) DADMU with stirring under the argon atmosphere. A reflux condenser was attached to the flask and the flask was transferred to a water bath. The contents of the flask were refluxed under argon with stirring for 2.5 hrs. at 80° C. The brown mixture was allowed to cool slowly to room temperature under argon overnight. A yellow brown precipitate was collected by suction filtration on a glass fritted filter (medium porosity). The precipitate was washed with four 15 ml portions of cold toluene to remove pyridine and a soluble brown impurity. The precipitated product was washed with three 30 ml portions of diethyl ether and dried overnight in the vacuum desiccator over CaSO₄. The product was then recrystallized from CH₃OH/diethyl ether under argon atmosphere to yield 0.529 of the yellow product Compound III (38% based on initial INC). The product had the following structure.

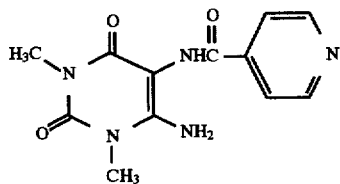

EXAMPLE IV

Preparation of 8-(4-pyridyl) theophylline: Compound IV

Compound III was readily cyclized to the corresponding theophylline species (Compound IV), by the following procedure.

To a 300 ml Ehrlenmeyer flask containing a stirbar were added 6.75 g (24 mmol) of Compound III and sufficient 2.5M aqueous NaOH (approximately 100 ml) to dissolve Compound III. The yellow-orange solution was heated with gentle stirring until boiling began. Gentle boiling was maintained for 30 min. during which time a precipitate began to separate. The solution was allowed to cool to room temperature and the pH was carefully adjusted to between 5 and 6 using 6M HCl (aq). During neutralization, the initial precipitate dissolved to an orange solution. As neutralization approached completion, reprecipitation occurred. The solution was cooled on the ice bath for 1 hr. and the pale yellow solid was collected by suction filtration on a glass fritted filter (medium porosity). The precipitate was washed with three 20 ml portions of diethyl ether. The crude product was dried over CaSO₄ overnight in a vacuum desiccator. The product was purified by recrystallization from dimethyl formamide (DMF). Crystals were collected by suction filtration as above and washed twice with 20 ml portions of ice cold isopropanol, followed by three 30 ml portions of diethyl ether. Drying was completed overnight in a vacuum desiccator. The yield was 1.87 g of metallic white crystals of Compound IV (30% based on initial amount of Compound III). Compound IV melted at 337.9°–339.5° C. to a clear orange liquid. Compound IV was analytically pure.

| C₁₂H₁₁N₅O₂ [257.17 g/mole] | | | | |
|---|---|---|---|---|
| | C | H | N | O |
| Theory | 56.04 | 4.28 | 27.24 | 12.44 |
| Found | 56.08 | 4.38 | 27.17 | 12.53 |

The product had the following structure.

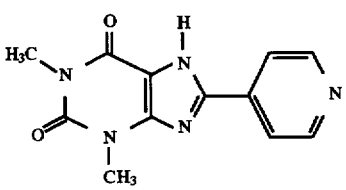

EXAMPLE V

Preparation of Fac-(bpy)Re(CO)₃[8-(4-pyridyltheophylline])-CF₃SO₃): Compound V

Into a 100 ml round bottom flask equipped with stirbar were added 150 mg (0.261 mmol) fac-(bpy)Re(CO)₃(O₃SCF₃), 250 mg (1.04 mmol) 8-(4-pyridyl)-theophylline and 40 ml of 2-methoxyethanol. 2-methoxyethanol was used as the solvent because 8-(4-pyridyl)-theophylline is insoluble in ethanol and water. After 15 min. of deaeration with argon, the solution was refluxed for 4 hrs. under argon atmosphere. After cooling, the solvent was removed by evaporation on a rotary evaporator. The solid was extracted with 20 ml methanol and filtered through a glass wool plug to remove insoluble 8-(4-pyridyl) theophylline ligand. The filtrate was chromatographed on a Sephadex LH-20 column (75 cm height×2 cm i.d.) using methanol as the eluant. Two bands were observed. The leading band (major product) was Compound V and was separated from a minor, unidentified impurity band (elution rate 0.1–0.2 ml/min.). Concentration of the fraction containing Compound V to 5 ml methanol volume on the rotary evaporator followed by reprecipitation in the 100 ml stirred diethyl ether gave Compound V as a pale lime-green powder. Compound V was collected by suction filtration on a glass fritted filter (medium porosity) and dried over $CaSO_4$ overnight in a vacuum desiccator. Yield=120 mg (42% based on fac-(bpy)Re(CO)$_3$(O$_3$SCF$_3$)). The product was analytically pure.

| $C_{26}H_{19}O_6F_3ReS$ [832.6 g/mole] | | | | |
|---|---|---|---|---|
| | C | H | N | O |
| Theory | 37.50 | 2.28 | 11.178 | 15.37 |
| Found | 38.19 | 2.53 | 11.77 | 15.78 |

The product had the following formula.

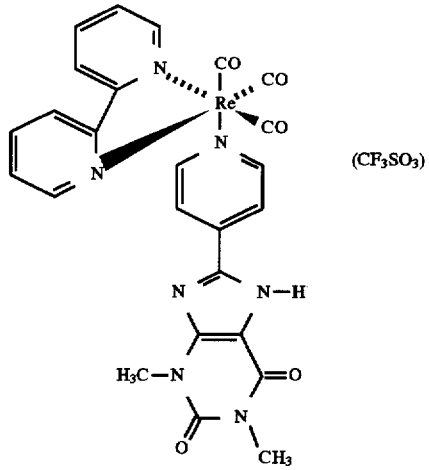

(CF$_3$SO$_3$)

EXAMPLE VI

Preparation of Fac-(bpy)Re(CO)$_3$[3-(4-pyridyl)-propionic acid] ClO$_4$.H$_2$O: Compound VI Into a 250 ml round bottom flask equipped with stirbar were added 300 mg (0.522 mmol) of fac-(bpy)Re(CO)$_3$CF$_3$SO$_3$, 79.2 mg (0.524 mmol) of 3-(4-pyridyl)-propionic acid, 70 ml of ethanol (absolute) and 30 ml of water. The mixture was deaerated with argon for 15 min and then refluxed for 4 hrs under argon atmosphere. The solution was cooled and the solvent was stripped. The residue was dissolved in the minimum amount of water, placed on a SP-25 Sephadex column, washed with water and eluted with 0.25M NaCl. The first yellow-green fraction was collected and the volume reduced to about 25 ml on the rotoevaporator. The contents of the flask were warmed with the heat gun and 1 ml of concentrated perchloric acid was added dropwise. Lime-green crystals formed. These were isolated by suction filtration on a 15 ml medium porosity fritted funnel, washed with a very small amount of ice water, and air dried for 30 min. The crystals were further dried in a vacuum desiccator over Drierite®.

| $C_{21}H_{17}O_9N_3ReCl$—H$_2$O [695.04 g/mol] | | | |
|---|---|---|---|
| | C | H | N |
| Theory | 36.29 | 2.76 | 6.05 |
| Found | 36.19 | 2.49 | 5.86 |

The product had the following formula.

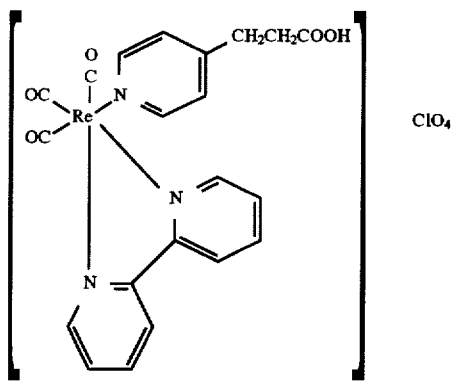

ClO$_4$

EXAMPLE VII

Electrochemiluminescence of Various Rhenium Compounds

The electrochemistry of various rhenium compounds was measured as 1 mM solutions in 10 ml of nitrogen-purged acetonitrile with 0.1M tetrabutylammonium tetrafluoroborate as a supporting electrolyte. The working electrode was a platinum disk obtained from Bioanalytical Systems, Inc., West Lafayette, Ind. A platinum wire was used as a counter electrode and a 1.0 mm silver wire served as the reference electrode. Measurements were made by scanning from −2.2 V to +2.2 V (vs SCE) at a scan rate of 100 mV/second. After each electrochemical measurement the potential difference between a Saturated Calomel Reference Electrode (SCE) and the silver wire was determined. Thus, the values reported are corrected to the potential vs SCE.

Electrochemiluminescent (ECL) measurements were made in aqueous solutions containing 0.1M phosphate-citrate buffer (pH 4.2), 25 mM oxalic acid, and 1% Triton® X-100. The electrode system used consisted of two platinum gauze (52 gauge) electrodes connected to a Radio Shack transistor socket (#276–548) by a 0.1 inch platinum wire. The electrodes were mounted on the outside of a 60 ml thick piece of cellulose acetate plastic. This plastic was machined so that a ¼ inch diameter hole allowed solution to flow easily between the working and counter-reference electrodes. The electrodes were connected to the potentiostat so that one electrode functioned as a working electrode (which was closer to the photomultiplier tube) and one electrode functioned as the counter and reference electrode. Measurements were made by sweeping from 1.5 V to 2.5 V (bias potention) at a scan rate of 50 mV/second. The ECL measurements are reported as the signal to noise ratio (or signal to background ratio) for a given concentration of compound. Background is defined as the luminescent counts observed with buffer and no ECL compounds added. Luminescent measurements were the peak light output observed during the first or second linear sweep.

Both electrochemiluminescent (ECL) and cyclic voltammetric measurements of each solution were performed with either a EG&G Model 273 potentiostat or an Oxford bipotentiostat (Ursar Scientific Instruments). The photon flux of each ECL measurement was monitored with a Berthold luminometer modified so that either a two or three electrode system could be placed in the 0.5 ml measuring solution. Both electrochemical and electrochemiluminescent measurements were recorded on a Kipp & Zonen Model BD 91 X, Y, Y' recorder.

Fluorescence measurements were made with 50 micromolar solutions on the desired compound in 3.0 ml of the previously described ECL buffer, or when insoluble in the buffer, in acetonitrile. Measurements were made on a Perkin-Elmer LS-5 Fluorescence Spectrophotometer. Prescans of the solutions' excitation and emission spectra were performed before the excitation an demission spectra were recorded so that the emission spectrum could be measured while irradiating at the maximum excitation wavelength and conversely, the excitation spectrum could be recorded while monitoring the maximum emission wavelength.

Table 2 summarizes the electrochemiluminescence data of several compounds.

TABLE 2

| Compound | $E_{ox}$ | $E_{red}$ | Fluorescence* | ECL (S/N) |
|---|---|---|---|---|
| Re (bpy)(CO)$_3$(4-Etpy) | 1.72 V | −1.18 V | (1) 400 nm (2) 565 nm | $2.0 \times 10^{-6}$ M (30.0) |
| Re(bpy)(CO)$_3$(py-C3H$_6$NHCO-C$_3$H$_6$-C$_8$-theophylline | N.D. | N.D. | (1) 421 nm (2) 567 nm | $2.2 \times 10^{-7}$ (8.2) |
| Re(4,4'-[Cl]$_2$-bpy)(CO)$_3$ | 1.79 V | N.D. | (1) 371 nm (2) 610 nm | $1.16 \times 10^{-7}$ M (71.9) |
| Re(4,4'-[Methyl]$_2$-bpy)(CO)$_3$(4-Etpy) | 1.72 V | N.D. | (1) 404 nm (2) 556 nm | $9.15 \times 10^{-8}$ M (5.5) |
| Re(4,4'-[Methoxy]$_2$-bpy)(CO)$_3$(4-Etpy) | 1.74 V | N.D. | (1) 395 nm (2) 568 nm | $1.08 \times 10^{-7}$ M (5.9) |
| Re(4,4'[(Et)$_2$N]$_2$-bpy)(CO)$_3$(4-Etpy) | 1.63 V | (Irreversible) | (1) 414 nm (2) 505 nm | $1 \times 10^{-7}$ M (2.0) |
| Re(4,4',5,5'-[Me]$_4$-bpy)(CO)$_3$(4-Etpy) | 1.77 V | N.D. | (1) 393 nm (2) 530 nm | $1.00 \times 10^{-7}$ M (2.6) |

*(1) Excitation; (2) emission.

The electrochemiluminescence was measured at the concentration shown and the results are expressed as the ratio of signal over background.

EXAMPLE VIII

Use of an Internal Standard for an ECL Based Assay

Several experiments were performed to investigate the use of an internal standard for electrochemiluminescence (ECL). The use of an internal standard for ECL measurements requires the addition of a second lumophor or "TAG" into the sample solution. One TAG is the calibrant or analyte and the second is the internal standard. Light emission from each TAG must be independently and simultaneously measured. One way to accomplish this is by using optical filters because the two TAGs emit at different wavelengths.

Materials and Equipment

The ECL from both the internal standard and the calibrant was measured in a "Flo-Thru" housing. The housing consists of a light-tight enclosure in which fluid and electrical connections are made to the electrochemical cell and the cell is aligned with a head-on photomultiplier tube. The light intensities were measured with a Hamamatsu photomultiplier (PMT) and an Oriel Model 7070 PMT detection system. The potentiostat was a Princeton Applied Research (PAR) Model 173 programmed with a PAR Model 175 (scanning between 1.8 and 1.0 V vs. Ag/AgCl at 100 mV/s). The electrochemical cell was a Bioanalytical Systems cell modified to accommodate a solution inlet and outlet port in the cell block. The working electrode material was gold which was embedded in the block. A stainless steel faceplate with a window for the PMT to the cell was used as the counter electrode. The reference electrode (Ag/AgCl) was external to the cell block and placed down stream. Fluid flow and sample introduction were performed manually using a peristaltic pump. Light intensity profiles were recorded on a Kipp & Zonen X-Y-Y recorder. Stock solutions of the TAGs were prepared by dissolving in the buffer. The buffer consisted of 0.15M phosphate, 0.10M tripropylamine, and 0.05% Tween 20 at pH 7.0.

Calibration Studies

The ECL of Os(bpy)$_3^{2+}$, OsTAG, was investigated. On scanning the potential in an anodic direction, two light emission profiles are observed. Light emission in the form of a plateau is observed near the formal potential of Os(bpy)$_3^{3+/2+}$ (0.8 V vs Ag/AgCl). The second emission occurs more positive at 1.46 V with a peaked shape. This second emission is much more intense and near the tripropylamine oxidation. The extrapolated detection limit was 100 pM (using a Hamamatsu R374 PMT).

The ECL of (Me$_4$bpy)Re(4-Et-pyr)(CO)$_3^+$, ReTag was investigated. The formal potential for oxidation is 1.7 V vs. Ag/AgCl (measured in acetonitrile by cyclic voltammetry). The ECL max is shifted positive (1.58 V) relative to OsTAG, which reflects the much more positive formal potential for oxidation. This material is of interest because it emits at 545 nm (water). The ReTAG emission is well separated in wavelength from that of Os(bpy)$_3^{2+}$(750 nm) and hence allows for optical separation using simple filters. The extrapolated detection limit of ReTAG was 100 pM (Hamamatsu R268 PMT).

Based on the ECL performance in the two procedures described, these compounds were used to test the possibility of using an internal standard for ECL. One criterion for an internal standard (OsTAG) is that it emit light independently of the calibrant TAG (ReTAG), i.e., the following quenching reaction should not occur:

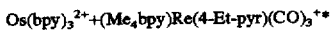

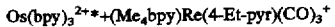

The following experiment was performed. At constant OsTAG concentration (1 micromolar), and varying ReTAG concentrations (0 to 100nM), the ECL of OsTAG was observed using an R268 PMT and LP 700 long pass filter. See FIG. 2. Within experimental error, no influence upon the OsTAG ECL by ReTAG was observed.

The same experiment was repeated except that the LP 700 was replaced with a short pass 620 filter to observe only the ReTAG ECL. The calibration curve for ReTAG is shown in FIG. 3. A calibration curve for ReTAG without OsTAG is also shown in FIG. 3. Again, within experimental error, the addition of OsTAG had no influence on the ReTAG ECL. The data indicate that Os(bpy)$_3^{2+}$ is well suited as an internal standard with ReTAG as the analyte.

EXAMPLE IX

Sensitivity of Detection of Electrochemiluminescence of Rhenium Labeled Rabbit Anti-Mouse Immunoglobulin G (IgG) Antibody The electrochemiluminescence of rabbit anti-mouse IgG antibody labeled with Fac-(bpy)Re(CO)$_3$[3-(4-pyridyl)-propionic acid]ClO$_4$.H$_2$O (Compound VI) (rhenium-labeled rabbit anti-mouse IgG antibody) is measured in a 15 ml three-neck, round bottom flask containing 10 ml of a solution prepared as described below; a 1.5 mm×10 mm magnetic stir bar; a 1.0 mm diameter silver wire quasi-reference electrode; a combination 28 gauge platinum wire counter electrode; and a working electrode consisting of a 22 gauge platinum wire welded to a 1 cm×1 cm square piece of 0.1 mm thick, highly polished platinum foil. (The working platinum foil electrode is shaped into a 3/16 of an inch diameter semi-circle surrounding the 28 gauge platinum wire counter electrode by 3/32 of an inch equidistantly).

The silver wire is connected to the EG&G Model 178 electrometer probe of the EG&G Model 173 potentiostat/galvanostat. The platinum wire counter electrode and the platinum working electrode are connected to the anode and cathode respectively of the EG&G Model 173 potentiostat. The device is grounded.

The electrochemiluminescence emitted from the rhenium-labeled rabbit anti-mouse IgG antibody solution is detected using an Hamamatsu R928 photomultiplier tube, set inside a Products for Research Model PR1402RF photomultiplier tube housing which is fitted with a Kodak #23A gelatin (red) filter. The photomultiplier tube housing is connected to an Oriel Model 7070 photomultiplier detection system.

Electrochemiluminescence is induced by pulsing for one second intervals, between zero and −2.0 volts cathodic potential. Electrochemiluminescent measurements are performed by integrating the resulting electrochemiluminescent photomultiplier tube signal using an integrator connected to a Microntra Model 22191 digital multimeter. The electrochemiluminescent signal is integrated for 10 seconds during the pulsing and recorded in millivolts.

A stock solution of 1.25×10$^{-7}$M rhenium-labeled rabbit anti-mouse IgG antibody is prepared from a concentrated solution (2 mg/ml, 7.5 Re/antibody) of the labeled antibody by dilution in phosphate-buffered saline (PBS). An aliquot of this solution (80 microliters) is added to 10 ml of dimethylsulfoxide (DMSO)/deionized, distilled water (1:1) containing 0.1M tetrabutylammonium tetrafluoroborate (TBABF$_4$) and 18 mM ammonium persulfate in the reaction vessel. The final rhenium-labeled antibody concentration is 1×10$^{-9}$M. Electrochemiluminescence is measured as described above.

Additional solutions representing various dilutions of the rhenium-labeled rabbit anti-mouse IgG antibody stock solution are made and aliquots (80 microliters) of these solutions are added to the same solution of rhenium-labeled antibody in the reaction vessel in increments which result in the following concentrations of labeled antibody: 5×10$^{-9}$M, 1×10$^{-8}$M, and 5×10$^{-8}$M. Electrochemiluminescence measurements are made for each solution as described. These results indicate the sensitivity of electrochemiluminescent detection of labeled antibody (1×10$^{-9}$M), and the dependence of the intensity of electrochemiluminescence on the concentration of the rhenium-labeled anti-mouse IgG antibody.

EXAMPLE X

Homogeneous Electrochemiluminescent Immunoassay for Antibody to Bovine Serum Albumin A solution containing 7.8×10$^{-6}$M bovine serum albumin (BSA) labeled with Fac-(bpy)Re(CO)$_3$[3-(4-pyridyl)-propionic acid]ClO$_4$.H$_2$O (Compound VI) (rhenium-labeled BSA) is prepared from a stock solution of rhenium-labeled BSA (2.5 mg/ml, 6 Re/BSA) by dilution in phosphate-buffered saline (PBS). 26 microliters of this solution are added to 10 ml of DMSO/deionized, distilled water (1:1) containing 0.1M TBABF$_4$ and 18 mM ammonium persulfate in the reaction vessel. The final rhenium-labeled BSA concentration is 2×10$^{-8}$M. Electrochemiluminescence is measured as described in Example IX.

In an analogous manner, a solution containing 7.8×10$^{-6}$M unlabeled BSA is prepared and added to the reaction vessel to give a final unlabeled BSA concentration of 5×10$^{-8}$M. The electrochemiluminescence of this solution and of a similar solution without BSA is measured.

A solution containing 3.75×10$^{-5}$M rabbit anti-BSA antibody is prepared from a stock solution of rabbit anti-BSA antibody (6.0 mg/ml) by dilution in PBS, and an aliquot (26 microliters) is added to the solution of rhenium-labeled BSA in the reaction vessel to give a final rabbit anti-BSA antibody concentration of 1×10$^{-7}$M.

The electrochemiluminescence of the resulting mixture of rhenium-labeled BSA antigen and antibody (rabbit anti-BSA) is measured. The results indicate a reduction in the electrochemiluminescence of the rhenium-labeled BSA upon addition of rabbit anti-BSA antibody and demonstrate that a homogeneous electrochemiluminescent detection of antibody to BSA may be achieved. Based upon these results one skilled in the art would know that a homogeneous electrochemiluminescent immunoassay for detecting other analytes of interest may be developed.

EXAMPLE XI

Heterogeneous Electrochemiluminescent Immunoassay for Legionella Using a Mouse Anti-Legionella Immunonoglobulin G (IgG) Antibody and Rhenium-Labeled Rabbit Anti-Mouse Immunoglobulin G (IgG) Antibody A formalinized suspension of the bacterium *Legionella micdadei* is adjusted to an optical density (at 425 nm) of 1.00 by dilution with PBS buffer. Approximately 3×10$^9$ cells are added to a conical microcentrifuge tube. The cells are centrifuged (10 minutes, 10,000 RPM), the supernatant decanted, and the cells resuspended in a 1:50 dilution of a mouse monoclonal IgG antibody, (1.45 mg/ml) specific for *Legionella midadei*, in PBS (1 ml). After incubation at room temperature for 1 hour, the cells are centrifuged, the supernatant decanted, the cells resuspended in PBS buffer and centrifuged again. Following decantation of the supernatant, the cells are resuspended in a 1:50 dilution (in PBS) of rabbit anti-mouse IgG antibody labeled with Fac-(bpy)Re(CO)$_3$[3-(4-pyridyl)-propionic acid]ClO$_4$ H$_2$O Compound VI, i.e., rhenium-labeled rabbit anti-mouse IgG antibody, (2 mg/ml, 7.5 Re/antibody). After incubation at room temperature for 1 hour, the cells are centrifuged, the supernatant decanted, and the cells resuspended in PBS and washed twice, with centrifugation, as before. Following the last wash the cells are resuspended in 200 microliters of PBS. 100 microliters of the cell suspension are added to the reaction vessel containing 10 ml of DMSO/deionized, distilled water (1:1) containing 0.1M TBABF$_4$ and 18 mM ammonium persulfate and transferred to the reaction vessel. The electrochemiluminescence is measured for the cell suspension. Another 100 microliters of the cell suspension are added to the reaction vessel and electrochemiluminescence measured. Electrochemiluminescence is measured for the solution without cells as a control according to the method described in Example IX. A heterogeneous electrochemiluminescent immunoassay for Legionella using rhenium-labeled rabbit anti-mouse IgG antibody can be successfully carried out.

EXAMPLE XII

Preparation of 2-[3-(4-methyl-2,2'-bipyridine-4'-propyl]-1, 3'dioxolane

Under an inert atmosphere of argon, 30 ml of dry tetrahydrofuran (THF) and 7.65 ml of dry di-isopropylamine (54.6 mmol) were added to a 3-neck, 600 ml flask via syringe with stirring. The solution was cooled to −78° C. by immersing the flask in a mixture of dry ice-isopropanol in a low form beaker. 21.6 ml of 2.5M n-butyl lithium (54 mmol) were slowly added to the flask. The resulting solution was stirred for 15 min and a solution of 9.58 g of 4,4'-dimethyl-2,2'-bipyridine (52 mmol) dissolved in 100 ml of dry THF was added dropwise by cannula with stirring over 1 hr.

The resulting brown mixture was further stirred at −78° C. for 2 hrs., 10 g of 2-(2-bromoethyl)-1,3-dioxolane (55 mmol) were added by syring and the resulting mixture stirred at −78° C. for 5 min. The reaction vessel was then placed in an ice bath (10° C.) and after 30 min began to change color. After 1 hr the color was dark violet, after 2 hrs the color was blue, after 2.5 hrs the color was green, and after 3.25 hrs the color was lemon yellow.

The reaction mixture was quenched with 30 ml of saturated NaCl followed by 10 ml of water and 50 ml of ether. The aqueous phase was extracted twice with 300 ml of ether and the combined ether phases were back-extracted with 100 ml of water and dried over anhydrous sodium sulphate.

To purify the reaction product, the sample was separated on alumina (Merck) 90. activity III, neutral. The eluants used were petroleum ether/diethyl ether (1:1) (the starting material elutes completely with petroleum ether/diethyl ether (2:1), followed by the product.

Proton NMR analysis confirmed that the structure of the isolated reaction product is

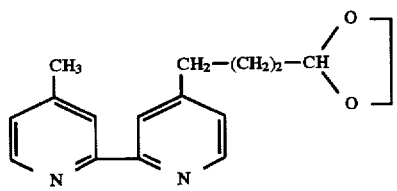

EXAMPLE XIII

Preparation and Purification of 4-butan-1-al)-4'-methyl-2, 2'bipyridine 2 g of 2-[3-(4-methyl-2,2'-bipyridine-4'-yl)-propyl]-1,3 dioxolane were dissolved in 50 ml of 1N Hcl and heated for 2 hrs at 50° C. The solution was cooled, adjusted to between pH 7 and 8 with sodium bicarbonate and extracted twice with 100 ml of chloroform.

The combined chloroform phases were washed with a small amount of water, dried over sodium sulfate, filtered and rotoevaporated to yield a yellow oil.

The yellow oil was purified on a silica gel column using ethyl acetate/toluene (1:1) as the eluant, the impurity being eluted with methanol.

Proton NMR analysis [δ1.96–2.11 (m,2H); 2.43 (s,3H); 2.46–2.50) (t,2H); 2.53–2.80 (M,2H); 7.12–7.14 (m,2H): 8.$^{h17-8}$.21 (br. s,2H); 8.52–8.58 (m,2H); 9.89 (s,1H)] confirmed that the structure of the reaction product is

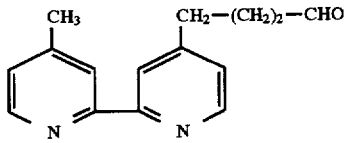

EXAMPLE XIV

Preparation of 4-(4-methyl-2,2'-bipyridine-4'-yl) butyric acid 0.5 g of 4-(butan-1-al)-4'-methyl-2,2'-bipyridine (2.0 mmol) were dissolved in 10 ml absolute acetone. 225 mg of finely powdered potassium permanganate (KMnO$_4$; 1.42 mmol) were added in portions to the solution with stirring. The reaction was followed by thin layer chromatography (silica; ethyl acetate/toluene 50:50), which indicated that while the aldehyde gradually disappeared a bipyridine of low R$_f$ was formed.

After the reaction reached completion, water was added and the MnO$_2$ was filtered and washed with small portions of Na$_2$CO$_3$ (aq.). The acetone was rotoevaporated and the residue extracted with CH$_2$Cl$_2$ to remove nonacidic bipyridines. The aqueous solution was made acidic by careful addition of 1.0N Hcl to pH 4.8. The solution became partially cloudy upon reaching this pH, the suspension redissolving at lower pH. The mixture was extracted five times with equal volumes of CH$_2$Cl$_2$, dried over Na$_2$So$_4$ and rotoevaporated to an oil which promptly solidified in vacuo. The crude solid was recrystallized from chloroform:petroleum ether to obtain white crystals.

Melting point: 103.5° C.–105.5° C.; IR: 1704 cm$^{-1}$. Proton NMR analysis was consistent with the following structure.

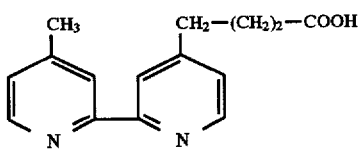

EXAMPLE XV

Modulation of Electroluminescent Signal Generated by Re(I)-Theophylline Conjugate Using Antibodies Specific for Theophylline Compound VI convalently bound to theophylline (Conjugate) is diluted to a final concentration of 150 nM using 0.1M phosphate buffer, pH 6.0. containing 0.35M sodium fluoride (PBF Buffer). Monoclonal antibody (clone number 9-49, ascites lot number WO399, cat number 046) specific for theophylline is obtained from Kallestad Laboratories, Inc. (Chaska, Minn.). The monoclonal antibody is diluted to different concentrations using PBF Buffer (between 21.9 micrograms of protein/ml to 700 micrograms/ml).

Another monoclonal antibody (control MAB) that is not reactive with theophylline is obtained from Sigma (St. Louis, Mo.) and is diluted to different concentrations between 21.9 micrograms of protein/ml to 700 micrograms/ ml using PBF Buffer. A standard solution of theophylline is prepared using theophylline obtained from Aldrich Chemical Co., (Milwaukee, Wis., cat number 26-140-8, M.W. 180.17). Theophylline is dissolved in PBF Buffer to give a final concentration of 75 micromolar and is diluted with PBF Buffer to 6 micromolar for use in assays. Prior to making electrochemiluminescence measurements a solution containing 250 mM oxalic acid and 5% (v/v) Triton-X 100 (ECl solution) is added to the reaction mixture. Measurements are made using a Berthold luminometer that is modified to allow the placement of two platinum gauze electrodes into the test tube containing the reaction solution. The electrodes are connected to a potentiostat and the electrochemiliminescence measurement is made by sweeping an applied potential across the electrodes from 1.5 to 2.5 volts at a scan rate of 50 mV/sec. The Berthold luminometer used for the measurement has a high gain, red sensitive photomultiplier tube. The luminometer output to the recorder is adjusted to $10^5$ counts/volt. The measurements are recorded on an X-Y-Y' recorder and the peak height is used as the measurement of electrochemiluminescence. The electrodes are cleaned between measurements by rinsing with a buffer at pH 4.2 containing 0.1M phosphate, 0.1 citrate, 0.025M oxalic acid, and 1% Triton X-100; pulsing the electrodes in this solution between +2.2 to −2.2 volts for 60 sec; and followed by −2.2 volts for 10 seconds. Next the electrodes are removed from this solution, rinsed in distilled water and wiped dry. The experiment is carried out as outlined below.

A solution of control monoclonal antibodies, antibodies to theophylline or PBF Buffer is added to a set of test tubes (Step 1). To the tubes, a solution of theophylline or PBF Buffer is added (Step 2). The solutions are mixed by briefly shaking the test tubes and allowing them to react for 25 min at room temperature. Then a solution of Conjugate is added to the tubes (Step 3). The test tubes are shaken and kept at room temperature for 15 min. Finally, 100 microliters of the ECL solution is added to each tube and electrochemiluminescence is measured as described above.

| Experimental Design for Studying the Effect of Antibody- Re(I)-theophylline conjugate (Conjugate) Interactions on Electroluminescence | | |
|---|---|---|
| Step 1 100 microliters of: | Step 2 200 microliters of: | Step 3 100 microliters of: |
| A. Control monoclonal antibody (2.19 micrograms to 70 micrograms) or | Buffer | Conjugate |
| B. Anti-theophylline antibody (2.19 micrograms to 70 micrograms) or | Buffer or Theophylline | Conjugate |
| C. PBF Buffer | Buffer | Conjugate or Buffer |

The experiment shows that a monoclonal antibody which specifically recognizes theophylline, when contacted with theophylline to which a rhenium compound (Compound VI) is attached, e.g., Re(I)-theophylline conjugate, will decrease the electrochemiluminescence. The decrease in electrochemiluminescence is proportional to the antibody concentration when the conjugate concentration is held constant. When an antibody is used which does not react with theophylline, only a slight decrease in the electrochemiluminescence is seen at the highest concentration of antibody.

The data also show that when theophylline is contacted with the anti-theophylline antibody and then the conjugate is added to the mixture, the amount of electrochemiluminescence is greater. This demonstrates that theophylline competes for the binding of antibody resulting in a greater amount of conjugate which can generate electrochemiluminescence.

EXAMPLE XVI

Assay for Theophylline in Serum Based on a Homogeneous Electrochemiluminescent Immunoassay Based on the results described in Example XV, a homogeneous immunoassay for theophylline is developed using antibody to theophylline and the Re(I)-theophylline conjugate (Conjugate) described in Example XV in a competitive binding format. The materials used are described in Example XV except the PBF buffer is 0.1M phosphate buffer, pH 6.0, containing 0.1M sodium fluoride. For this assay, a specific concentration of monoclonal antibody to theophylline is chosen. The antibody concentration is 55 micrograms/ml. The conjugate concentration is adjusted to 175 nM. Theophylline is added to human serum to give final concentrations of 2.5, 5, 10, 20 and 40 micrograms of theophylline/ml of serum.

The assay is performed by adding 10 microliters of serum to 290 microliters of anti-theophylline monoclonal antibody and holding the solution at room temperature for 25 min. Then 100 microliters of conjugate were added to each tube to give a final concentration of 35 nM and this solution is held at room temperature for 15 min. 100 microliters of the ECL solution described in Example 34 are then added to each tube and electrochemiluminescent properties of the solutions are measued as previously described using a sweep mode for 1.5 volts to 2.5 volts at 50 mV/sec. The results demonstrate that there is a correlation between the concentration of theophylline in a serum sample and the amount of electrochemiluminescence that is emitted by the reaction mixture. This observation demonstrates that it is possible to develop an assay for theophylline.

Based on these results, one skilled in the art would be able to develop a homogeneous electrochemiluminescent immunoassay for detecting and quantifying an analyte of interest in a biological matrix.

EXAMPLE XVII

Assay for Theophylline in Hemolyzed, Lipemic, Icteric and Normal Serum Samples Based on a Homogeneous Electrochemiluminescent Immunoassay and Comparison to a Fluorescence Polarization Assay The concentration of theophylline in different types of serum samples is determined using a homogeneous electrochemiluminescent immunoassay. The format for the assay is a competitive binding assay using a monoclonal antibody specific for theophylline and the Conjugate described in Example XV. The reagents and methods for electrochemiluminescence are described in the previous example.

The fluorescence polarization assay used to measure the concentration of theophylline in the different serum samples is carried out using an automated TDX instrument from Abbott Laboratories (North Chicago, Ill.). Hemolyzed, lipemic, icteric and normal sera were used in the assays and data for the abnormal sera are listed below.

| Homogeneous Theophylline Assay Characteristics of Potentially Problematic Serum | | |
|---|---|---|
| Serum | Factor Concentration | Normal Range |
| Hemolyzed | 12.4 mg/dl hemoglobin | 0–3.2 mg/dl |
| Lipemic | 405 mg/dl triglycerides | 10–190 mg/dl |
|  | 196 mg/dl cholesterol | 120–200 mg/dl |
| Icteric | 10 mg/dl bilirubin | 0–1.5 mg/dl |

Different amounts of theophylline are added to the serum samples to give final concentrations between 2.5 micrograms theophylline/ml and 40 micrograms theophylline/ml. Data are obtained for the homogeneous electrochemiluminescent immunoassay.

Each serum sample is also analyzed for the concentration of theophylline by a fluorescence polarization assay. The concentration of theophylline measured by the homogeneous electrochemiluminescence immunoassay and the fluorescence polarization assay are compared. The data are plotted as a scattergram. The data points are analyzed by linear regression and the correlation coefficients are calculated. The analysis demonstrates an excellent correlation between the two assays. The correlation coefficients (r) are high. The slopes of the curves for normal, hemolyzed, and lipemic serum samples are between 0.8 and 1.2, demonstrating excellent recovery of theophylline from these serum samples.

Although the electrochemiluminescence emitted by the icteric serum samples containing theophylline are higher than for the other serum samples, it is proportionally higher at each theophylline concentration. The correlation coefficient is high for the data points comparing electrochemiluminescence and fluorescence polarization; however, the slope demonstrates higher recovery for the theophylline in the icteric serum sample.

Based on these results, the concentration of theophylline in an icteric sample may be determined by establishing a standard curve for the sample by adding known amounts of the Conjugate to aliquots of the icteric serum. These data demonstrate that a homogeneous electrochemiluminescent immunoassay may be used to measure the concentration of theophylline present in serum samples containing abnormal levels of hemoglobin, lipid and bilirubin.

A homogeneous electrochemiluminescent immunoassay offers advantages over a fluorescence polarization method because of the versatility of ECL detection, i.e., more sensitive detection at higher concentrations of biological molecules.

A homogenous electrochemiluminescent immunoassay offers further advantages over a fluorescence polarization method because no incident light source is required; electrical excitation being the only requirement for efficient light-generation. Consequently, no sophisticated optics are necessary. Since the measurement principle is purely specific photon emission induced by electrochemical stimulation, the sensitivity of the system is potentially much greater than fluorescence polarization and a wider dynamic range will be achievable. Also, measurement of a much greater variety of analytes is possible with a homogeneous electrochemiluminescent immunoassay than is provided by the fluorescence polarization and a wider dynamic range will be achievable. Also, measurement of a much greater variety of analytes is possible with a homogeneous electrochemiluminescent immunoassay than is provided by the fluorescence polarization technique, due to the selective modulation of electrically-stimulated chemiluminesence by biomolecular recognition events, e.g., antibody-antigen interactions.

Based on these results, one skilled in the art would know that homogeneous electrochemiluminescent immunoassays for detecting other analytes of interest in abnormal serum samples may be developed.

EXAMPLE XVIII

Assay for Theophylline in Serum Based on a Heterogeneous Electrochemiluminescent Assay Using an immunometric assay format, a heterogeneous assay for theophylline is developed using a Compound VI labeled anti-theophylline antibody and theophylline BSA immobilized on Biomag magnetic particles. The antibody concentration is 20 micrograms/ml. The magnetic particle concentration is 1% solids (wt/vol). Theophylline is added to a final concentration of 10 and 40 micrograms/ml of serum. The theophylline serum standards are diluted 1000 fold in PBF Buffer (sodium phosphate buffer, pH 7.0. 0.1M sodium fluoride) containing 0.1% BSA.

The assay is performed by the addition of 75 microliters of the diluted serum standards to 75 microliters of antibody conjugated to Compound VI and incubating the solution at room temperature for 20 min. Then 50 microliters of the theophylline-BSA-Biomag particles are added and the suspension is allowed to stand for 5 min. The particles are separated magnetically and 100 microliters of the supernatant are measured for electrochemiluminescence.

Based on the results, one skilled in the art would be able to develope a heterogeneous electrochemiluminescence immunoassay for other analytes of interest in a biological matrix.

EXAMPLE XIX

Labelling DNA with an Electrochemiluminescent Moiety

The following method has been used to label DNA with an electrochemiluminescent moiety.

1.0 $A_{260}$ of the custom synthesized 38 mer (MBI 38)

TCACCAATAAACCGCAAACACCATCCCGTCCTGCCAGT* where T* is thymidine modified at carbon 5 with

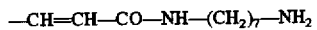

—CH=CH—CO—NH—(CH$_2$)$_7$—NH$_2$ are dissolved in 100 microliters of 0.01M phosphate buffer, pH 8.7. 100 microliters of a solution of fac-(bpy)Re(CO)$_3$ [3-(4-bipyridyl)-propionic acid]ClO$_4$.H$_2$O (Compound VI) (2.3 mg in 300 microliters of 0.01M potassium phosphate buffer, pH 8.7) are added. The contents are stirred and allowed to stand at room temperature overnight.

100 microliters of a saturated aqueous solution of sodium borohydride are added to the mixture to convert the reversible imine Schiff's base linkage into non-reversable amine linkage. The reaction is allowed to run at room tempertuer for 2 hrs. The solution is then treated carefully with a few drops of dil. acetic acid to quench excess of sodium borohydride. The reaction solution is loaded into a P-2 gel filtration column (18 inches×½ inch) which is preequilibrated with 0.1M triethylammonium acetate, pH 6.77. The column is eluted with the same buffer and 2 ml fractions are collected at a flow rate of 20 ml/hr. DNA eluted in fractions 9 and 10 are well separated from unreacted rhenium complex. The collected DNA sample exhibits typical UV absorption and additionally shows fluorescent emission spectrum when excited. The fluorescent emission shows the presence of the rhenium moiety in the DNA sample. The product travels as single fluorescent band on polyacrylamide gel electrophoresis. The electrophoretic mobility of the labeled DNA (MBI 38-Compound VI Conjugate) is approximately the same as the unlabeled DNA.

EXAMPLE XX

Electrogenerated Chemiluminescent Properties of Labeled DNA

The labeled DNA sample from Example XIX, Synthesis A (MBI 38-Compound I) is used to study its electrochemiluminescent properties. Various concentrations of labeled DNA are dissolved in 0.5 ml of 0.1M phosphate buffer, pH 4.2, containing 0.1M citrate, 25 mM oxalate and 1.0% Triton X-100 and measured on a modified Berthold luminometer. The electroluminescent signal is responsive to various DNA concentrations.

EXAMPLE XXI

Hybridization Studies of Compound VI-Labeled Oligonucleotide

The complementary strand to the 38 mer described in Example XX is synthesized using the ABI model 380 B DNA synthesizer and is designated MGEN-38.

To determine if the covalent attachment of Compound I to the oligonucleotide affected the hybridization properties of the MBI 38 oligonucleotide, the following experiment is devised. Various concentrations of the target fragment (MGEN-38) are spotted on a sheet of Gelman RP nylon membrane, fixed and probed with either MBI 38 or MBI 38-Compound VI. Both fragments are treated with T4 polynucleotide kinase and gamma $^{32}$P[ATP] and labeled with $^{32}$P at the 5' end. The hybridization sensitivities of DNA and Compound VI-labelled DNA are then compared.

Concentrations of MGEN-38 DNA, ranging from 50 ng down to 0.05 ng, are spotted on a nylon membrane and allowed to air dry. Duplicate membranes are set up. The blots are treated for 2 min each in: 1.5M NaCl-0.5 NaOH to fully denature the DNA; 1.5M, NaCl-0.5M TRIS to neutralize the blot, and finally in 2×SSC. The blot is baked in a vacuum oven at 80° C. for 2 hrs.

The hyrbridization probe is prepared as follows: 3 micrograms of MBI 38 and MBI 38-Compound I are kinased with 10 units of T4 kinase and 125 microcuries of gamma $^{32}$P-ATP. The percentage of isotope incorporation into DNA is determined.

Prehybridization and hybridization solutions are prepared according to Maniatis (24). Blots are prehybridized for 4 hrs. at 53° C. with 50 micrograms/ml of calf thymus DNA. The blots are then placed in hybridization solution containing the respective probes at 10,000,000 cpm, and allowed to hybridize overnight (12 hrs) at 53° C. The following day, the blots are washed as follows:

twice with 2×SSC+0.1% SDS at 53° C. for 15 minutes each wash twice with 0.2×SSC+0.1% SDS (same as above)

twice with 0.16%×SSC+0.1% SDS (same as above)

The blots are then air dried and exposed to Kodak X-omat film at −70° C.

Analysis of the X-ray shows that very similar hybridization patterns are observed between the MBI 38 and MBI 38-Compound VI probe. In both cases hybridization of probe to 0.5 ng of target is observed, and faint traces of hybridization are observed down to 0.05 ng of target DNA. No hybridization activity by the probe is detected for the negative control DNA (phage lambda DNA spotted at 50 ng).

EXAMPLE XXII

The 38-mer E. coli probe labeled with

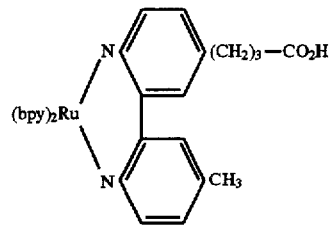

as described in Example XXI was hybridized with a sample of E. coli nucleic acids according to Maniatis [Maniatis, T., Fritsch, E. F. and Sambrook, J., Molecular Cloning: A laboratory manual, p. 150–160. Cold Spring Harbor Press, Cold Spring Harbor, N.Y. (1982)]. The hybridized complex was then captured by another solid support bound probe complementary to another sequence of E. coli DNA adjacent to the signal probe. The capture procedure used the same hybridization conditions as used for the first part of this protocol. The hybridized complex was separated from the single stranded nucleic acids by centrifugation and repeated washings. The isolated complex was then heated at 100° C. in water for 5 min. to dissociate the complex. The labeled probe now released into solution was transferred into appropriate cocktail for measurement of electrochemiliminescent signal. The intensity of the signal corresponded to the quantity of the target DNA in a linear fashion.

A sample of aminolinked DNA (a 38-mer containing 15 nucleotide consensus sequence from E. coli) was dissolved in 100 ul of 0.01M phosphate buffer, pH 8.7.100 ul of a solution of the osmium complex

(2.3 mg in 300 microliters of 0.01M potassium phosphate buffer, pH 8.7) were added. The contents were stirred and allowed to stand at room temperature overnight.

100 microliters of a saturated aqueous solution of sodium borohydride was added to the mixture to convert the reversible imine Schiff's base linkage into non-reversible amine linkage. The reaction was allowed to run at room temperature for 2 hr. The labeled probe was purified by gel filtration chromatography. The labeled DNA probe exhibited spectroscopic properties consistent with attachment of the osmium complex.

The probe labeled with osmium complex was hybridized with a sample of E. coli nucleic acids according to Maniatis, supra. The hybridized complex is then captured by another solid support bound probe complementary to another sequence of E. coli DNA adjacent to the signal probe. The capture procedure uses the same hybridized conditions as used for the first part of this protocol. The hybridized complex is separated from the single stranded nucleic acids by centrifugation and repeated washings. The isolated complex is then heated at 100° C. in water for 5 min. to dissociate the complex. The labeled probe now released into solution is transferred into appropriate cocktail for measurement of electrochemiluminescent signal. The intensity of the signal corresponds to the quantity of the target DNA in a linear fashion.

The rhenium complex

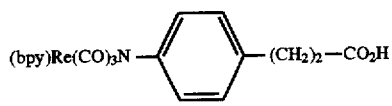

is first converted into an N-hydroxysuccinimide derivative by dissolving 3 mg in 60 microliters of anhydrous dimethylformamide and treating it with a solution of N-hydroxysuccinimide (52 mg) in 200 microliters of anhydrous DMF in the presence of 94 mg dicyclohexylcarbodiimide (DCC). The reaction is allowed to proceed for 4 hrs at 0° C. Precipitated dicyclohexylurea is removed by centrifugation and the supernatant (200 microliters) is added to the solution of amino-linked DNA (a 38-mer containing 15 nucleotide consensus sequence from E. coli) in 0.01M phosphate buffer pH 8.77 ($2A_{260}$ in 100 microliters of buffer). The reaction is allowed to proceed overnight at room temperature. A considerable amount of solid appears in the reaction which is removed by filtration through glass wool. The filtrate is concentrated and dissolved in 0.5 ml of 1M triethylammonium acetate (pH 6.8). The reaction mixture is then chromatographed on a gel filtration column. The labeled DNA probe exhibits spectroscopic properties consistent with attachment of the rhenium complex (em 594 nm).

The proble labeled with rhenium is hybridized with a sample of E. coli nucleic acids according to Maniatis, supra. The hybridized complex is then captured by another solid support bound probe complementary to another segment of E. coli DNA adjacent to the signal probe. The capture procedure uses the same hybridization conditions as used for the first part of this protocol. The hybridized complex is separated from the single stranded nucleic acids by centrifugation and repeated washings. The isolated complex is then heated at 100° C. in water for 5 min. to dissociate the complex. The labeled probe now released into solution is transferred into appropriate cocktail for measurement of electrochemiluminescent signal. The intensity of the signal corresponds to the quantity of the target DNA in a linear fashion.

The 38-mer DNA probe from E. coli independently labled with ruthenium, rhenium and osmium complexes is used in separate experiments to hybridize with its complementary sequences. The electrochemiluminescent signal of the duplex is compared with electrochemiluminescent signal of the corresponding labeled single-stranded probe. A modulation of the electrochemiluminescent signal is observed in each case for the duplex.

References:
(1) Weber, S. G. , et al., "Photoelectroanalytical Chemistry: Possible Interference in Serum and Selective Detection of Tris (2,2'-bypyridine) ruthenium(II) in the Presence of Interferents." Clinical Chemistry 29:1665–1672 (1983).
(2) Rubinstein, I., and Bard, A. J., "Electrogenerated Chemiluminescence. 37. Aqueous ECL Systems Based on Ru (2,2'-bypyridine)$_3^{2+}$ and Oxalate or Organic Acids." J. Am. Chem. Soc. 103:512–516 (1981).
(3) White, H. S., and Bard, A. J., "Electrogenerated Chemiluminescence. 41. Electrogenerated Chemiluminescence and Chemiluminescence of the Ru (2,2-bpy)$_3^{+2}$—$S_2O_8^{-2}$ System in Acetonitrile-Water Solutions," J. Am. Chem. Soc. 104:6891 (1982).
(4) Curtis et al., "Chemiluminescence: A New Method for Detecting Fluorescent Compounds Separated by Thin Layer Chromatography." J. Chromatography 134:343–350 (1977).
(5) Sprintschnik, G., et al., "Preparation and Photochemical Reactivity of Surfactant Ruthenium (II) Complexes in Monolayer Assemblies and at Water-Solid Interface," J. Am. Chem. Soc. 99:4947–4954 (1977).
(6) Minnich, S. A., et al., "Enzyme Immunoassay for Detection of Salmonellae in Foods, " Appln. and Environ. Micro. 43:1124–1127 (1982).
(7) Thomason, B. M., "Current Status of Immunofluroescent Methodology for Salmonellae," J. Food Prot. 44:381–384 (1981).
(8) Mattingly, J. A., "An Enzyme Immunoassay for the Detection of All Salmonella Using a Combination of a Myleloma Protein and a Hybridoma Antibody," J. Immunol. Meth. 73:147–156 (1984).
(9) Thompson, N. E., et al., "Detection of Staphylococcal enterotoxins by enzyme-linked immunosorbent assays and radio-immunoassays: Comparision of monoclonal and polyclonal antibody systems," Appln. and Environ. Micro., submitted publication.
(10) American Public Health Association, Standard methods for the examination of water and wastewater. 15th ed. American Public Health Association, Inc., New York (1980).
(11) American Public Health Association, Compendium of methods for the microbiological examination of foods. American Public Health Association, Washington, D.C. (1976).
(12) Clark, H. F., Geldreich, E. E., Lester, H. L., and Kabler, P. W., "The membrane filter in sanitary microbiology," Public Health Rep. 66:951–957 (1951).
(13) Feng, P., and Hartman, P. A., "Fluorogenic assays for immediate confirmation of Escherichia coli.," Appl. Environ. Microbiol. 43:1320–1329 (1982).
(14) Geldreich, E. E., "Standard method Revisions (16th edition) for Conventional coliform Procedures." In: New developments in drinking water microbiology workshop, 85th Annual Meeting of the American Society for Microbiology (1985).
(15) Hussong, D., Colwell, R. R., and Weiner, R. M., "Rate of occurrence of false-positive results from total coliforms most-probable-number analysis of shellfish and estuaries," Appln. Environ. Microbiol 40:981–983 (1980).
(16) Hussong, D., Demare, J. M., Weiner, R. M., and Colwell, R. R., "Bacteria associated with false-positive most-probable-number coliform test results for shellfish and estuaries," Appln. Environ. Microbio. 41:35–45 (1981).
(17) Lin, S., "Evaluation of coliform tests for chlorinated secondary effluents," J. Water Pollut. Control Fed. 45:498–506 (1973).
(18) Mckee, J. E., McLaughlin, R. T., and Lesgourgues, P., "Application of molecular filter techniques to the bacterial assay of sewage III. Effects of physical and chemical disinfection," Sewage Ind. Waste 30:245–252 (1958).
(19) Mead, J. A. R., Smith, J. N., and Williams, R. T., "The biosynthesis of the glucuronides of umbelliferone and 4-methylumbelliferone and their use in fluorimetric determination of betafluoronidase," Biochem. J. 61:569–574 (1954).
(20) Olson, B. H., "Enhanced accuracy of coliform testing in seawater by modification of the most-probable-number method," Appl. Environ. Microbiol. 36:438–444 (1978).
(21) Presnell, M. W., "Evaluation of membrane filter methods for enumerating coliforms and fecal coliforms in estuarine waters," Proc. National Shellfish Sanitation Workshop 1974:127–131 (1974).
(22) Presswood, W. G. and Strong, D. K., "Modification of mFC medium by eliminating rosolic acid," Appl. Environ. Microbiol. 36:90–94 (1978).

(23) Warr, G. W., and Marchalonis, J. J., "Purification of Antibodies," *Antibody as a Tool*, J. Wiley and Sons, New York, 59–96 (1982).

(24) Maniatis, T., Fritsch, E. F., and Sambrook, J., *Molecular Cloning: A Laboratory Manual*, 150–160. Cold Spring Harbor Press, Cold Spring Harbor, N.Y. (1982).

What is claimed is:

1. A method for calibration of an electrochemiluminescent assay system using an internal standard, comprising the steps of:
   (1) forming a solution containing
      (a) an analyte comprising a first electrochemiluminescent moiety, and
      (b) an internal standard comprising a second electrochemiluminescent moiety, said first and second moieties having electrochemiluminescent characteristics substantially independent of one another such that the analyte and the internal standard can be induced to electrochemiluminesce independent of each other, and having electrochemiluminescent emissions at sufficiently different wavelengths that each can be differentiated from the other, and
   (2) independently measuring electrochemiluminescence emitted by the analyte and electrochemiluminescence emitted by the internal standard,
   wherein the analyte is a moiety having the formula $(Re(P)_m(L^1)_n(L^2)_o(L^3)_p(L^4)_q(L^5)_r(L^6)_s)_t(B)_u$ wherein
   P is a polydentate ligand of Re; $L^1$, $L^2$, $L^3$, $L^4$, $L^5$ and $L^6$ are ligands of Re, each of which is the same as or not the same as each other ligand;
   B is a substance which is a ligand of Re or is conjugated to one or more of P, $L^1$, $L^2$, $L^3$, $L^4$, $L^5$ or $L^6$;
   m is an integer equal to or greater than 1; each of n, o, p, q, r and s is zero or an integer; t is an integer equal to or greater than 1; and u is an integer equal to or greater than 1;
   P, $L^1$, $L^2$, $L^3$, $L^4$, $L^5$, $L^6$ and B being of such composition and number that the chemical moiety can be induced to electrochemiluminesce and the total number of bonds to Re provided by the ligands of Re being equal to the coordination of Re;
   and the internal standard is an osmium containing moiety.

2. A method according to claim 1 wherein the internal standard is $Os(bpy)_3^{2+}$.

3. A method according to claim 1 wherein
   P is $Me_4bpy$, m is 1
   L1 is (4-Et-pyr), n is 1
   L2, L3, and L4 are each CO, o, p, and q are each 1, and r and s are each 0.

4. A method according to claim 3 wherein the internal standard is $Os(bpy)_3^{2+}$.

5. A method for calibration of an electrochemiluminescent assay system using an internal standard, comprising the steps of:
   (1) forming a solution containing
      (a) an analyte comprising a first electrochemiluminescent moiety, and
      (b) an internal standard comprising a second electrochemiluminescent moiety, said first and second moieties having electrochemiluminescent characteristics substantially independent of one another such that the analyte and the internal standard can be induced to electrochemiluminesce independent of each other, and having electrochemiluminescent emissions at sufficiently different wavelengths that each can be differentiated from the other, and
   (2) independently measuring electrochemiluminescence emitted by the analyte and electrochemiluminescence emitted by the internal standard,
   wherein the analyte is a moiety having the formula

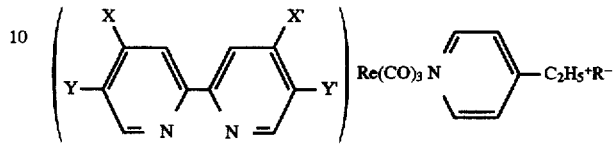

wherein X and X' may be the same or different and are selected from the group consisting of H, $N(C_2H_5)_2$, $CH_3$, $CH_3O$, $C_6H_5$, Cl, $CO_2CH_3$, CN, and $NO_2$, and Y and Y' may be the same or different and are either H or $CH_3$, provided that if X and X' are the same and Y and Y' are the same and X is $CO_2CH_3$, then Y is not H and, further provided that if X and X' are the same and Y and Y' are the same, then X and Y are not H; and R is an anion;
   and the internal standard is an osmium containing moiety.

6. A method according to claim 5 wherein the internal standard is $Os(bpy)_3^{2+}$.

7. A method according to claim 5 wherein X, X', Y and Y' are each $CH_3$.

8. A method according to claim 7 wherein the internal standard is $Os(bpy)_3^{2+}$.

9. A method for calibration of an electrochemiluminescent assay system using an internal standard, comprising the steps of:
   (1) forming a solution containing
      (a) an analyte comprising a first electrochemiluminescent moiety, and
      (b) an internal standard comprising a second electrochemiluminescent moiety, said first and second moieties having electrochemiluminescent characteristics substantially independent of one another such that the analyte and the internal standard can be induced to electrochemiluminesce independent of each other, and having electrochemiluminescent emissions at sufficiently different wavelengths that each can be differentiated from the other, and
   (2) independently measuring electrochemiluminescence emitted by the analyte and electrochemiluminescence emitted by the internal standard,
   wherein the analyte is a moiety having the formula $(Re(P)_m(L^1)_n(L^2)_o(L^3)_p(L^4)_q)_t(B)_u$ wherein
   P is a bidentate aromatic heterocyclic nitrogen-containing ligand of Re selected from the group consisting of bipyridyl, substituted bipyridyl, bipyrazyl, substituted bipyrazyl, phenanthrolyl and substituted phenanthrolyl, wherein each of said substituted groups is substituted by an alkyl, aryl, aralkyl, carboxylate, carboxaldehyde, carboxamide, cyano, amino, hydroxycarbonyl, hydroxyamino, aminocarbonyl, amidine, guanidinium, ureide, sulfur-containing group, phosphorous-containing group, or the carboxylate ester of N-hydroxysuccinimide; $L^1$, and $L^2$, independently of one another, each is a bidentate aromatic heterocyclic nitrogen-containing ligand of Re selected from the group consisting of bipyridyl, substituted bipyridyl, bipyrazyl, substituted bipyrazyl, phenanthrolyl and substituted phenanthrolyl, wherein each of said substituted groups is substituted by an alkyl, aryl, aralkyl, carboxylate, carboxaldehyde, carboxamide, cyano, amino, hydroxycarbonyl, hydroxyamino, aminocarbonyl, amidine, guanidinium, ureide, sulfur-containing group, phosphorous-containing group, or the carboxylate ester of N-hydroxysuccinimide; or is a monodentate ligand selected from the group consisting of carbon monoxide cyanides, isocyanides, halides, and alphatic, aromatic and heterocyclic phosphines, amines, stilbines, and arsines; and each of $L^3$, and $L^4$ is a monodentate ligand selected from the group consisting of carbon monoxide, cyanides, isocyanides, halides, alphiatic, aromatic and heterocyclic phosphines, amines, stilbines, and arsines;

each of P, $L^1$, $L^2$, $L^3$ and $L^4$ being the same or not the same as each other ligand;

B is a whole cell, subcellular particle, polypeptide, nucleic acid, polysaccharide, alkaloid, steroid, vitamin, amino acid, or nonbiological polymer which is conjugated to one or more of P, $L^1$, $L^2$, $L^3$ and $L^4$;

M is an integer equal to or greater than 1;

each of n, o, p and q is zero or an integer;

t is an integer equal to or greater than 1;

P, $L^1$, $L^2$, $L^3$, $L^4$ and B being of such composition and number that the chemical moiety can be induced to electrochemiluminescence and the total number of bonds to Re provided by the ligands of Re being equal to the coordination number of Re and the internal standard is an osmium containing moiety.

10. A method according to claim 9 wherein the internal standard is $Os(bpy)_3^{2+}$.

11. A method according to claim 9 wherein

P is $Me_4bpy$, m is 1

L1 is (4-Et-pyr), n is 1

L2, L3, and L4 are each CO, o, p, and q are each 1.

12. A method according to claim 11 wherein the internal standard is $Os(bpy)_3^{2+}$.a

* * * * *